US010201429B2

United States Patent
Enomoto et al.

(10) Patent No.: US 10,201,429 B2
(45) Date of Patent: Feb. 12, 2019

(54) ARTIFICIAL KNEE JOINT IMPLANT

(71) Applicant: KYOCERA Medical Corporation, Osaka-shi, Osaka (JP)

(72) Inventors: Yuichi Enomoto, Osaka (JP); Masahiko Hashida, Osaka (JP)

(73) Assignee: Kyocera Corporation, Kyoto (JP)

( * ) Notice: Subject to any disclaimer, the term of this patent is extended or adjusted under 35 U.S.C. 154(b) by 0 days.

(21) Appl. No.: 15/329,796

(22) PCT Filed: Oct. 5, 2015

(86) PCT No.: PCT/JP2015/078178
§ 371 (c)(1),
(2) Date: Jan. 27, 2017

(87) PCT Pub. No.: WO2016/063714
PCT Pub. Date: Apr. 28, 2016

(65) Prior Publication Data
US 2017/0266013 A1    Sep. 21, 2017

(30) Foreign Application Priority Data

Oct. 21, 2014 (JP) .................................. 2014-214618

(51) Int. Cl.
*A61F 2/38*    (2006.01)
*A61F 2/30*    (2006.01)

(52) U.S. Cl.
CPC .............. *A61F 2/3868* (2013.01); *A61F 2/38* (2013.01); *A61F 2/389* (2013.01); *A61F 2/3859* (2013.01);

(Continued)

(58) Field of Classification Search
CPC ........ A61F 2/38; A61F 2/3868; A61F 2/3859; A61F 2/389
See application file for complete search history.

(56) References Cited

U.S. PATENT DOCUMENTS 5,935,173 A * 8/1999 Roger ................... A61F 2/3868
623/20.31
6,123,729 A * 9/2000 Insall ................... A61F 2/3859
623/20.31

(Continued)

FOREIGN PATENT DOCUMENTS

JP    2000-116682 A    4/2000
JP    2007-509709 A    4/2007

(Continued)

OTHER PUBLICATIONS

International Search Report, PCT/JP2015/078178, Dec. 15, 2015, 2 pgs.

*Primary Examiner* — Alvin Stewart
(74) *Attorney, Agent, or Firm* — Volpe and Koenig, P.C.

(57) ABSTRACT

In an artificial knee joint implant, an increase in constraint force of a femur component and a tibia component in the anterior-posterior direction and the left-right direction of a patient is enabled, and an increase in an allowable degree of medial pivot motion is enabled. An artificial knee joint implant has a femur component to be fixed to a distal portion of a femur of a patient, and a tibia component to be fixed to a proximal portion of a tibia of the patient. Femur sliding faces of the femur component and tibia sliding faces of the tibia component each include a region in which the curvature radius varies in a predetermined direction.

9 Claims, 20 Drawing Sheets

(52) U.S. Cl.
CPC ............... *A61F 2002/30159* (2013.01); *A61F 2002/30327* (2013.01); *A61F 2002/30934* (2013.01)

(56) References Cited

U.S. PATENT DOCUMENTS

| | | | | |
|---|---|---|---|---|
| 6,152,960 | A * | 11/2000 | Pappas | A61F 2/38 623/20.31 |
| 7,261,740 | B2 | 8/2007 | Tuttle et al. | |
| 7,364,590 | B2 * | 4/2008 | Siebel | A61F 2/38 623/20.35 |
| 8,192,498 | B2 * | 6/2012 | Wagner | A61F 2/38 623/20.21 |
| 8,236,061 | B2 * | 8/2012 | Heldreth | A61F 2/38 623/20.14 |
| 8,298,288 | B2 * | 10/2012 | Walker | A61F 2/3886 623/20.21 |
| 8,932,365 | B2 * | 1/2015 | Parisi | A61F 2/3886 623/20.27 |
| 9,168,145 | B2 * | 10/2015 | Wyss | A61F 2/3886 |
| 9,308,095 | B2 * | 4/2016 | Parisi | A61F 2/3859 |
| 9,642,711 | B2 * | 5/2017 | Carson | A61F 2/3886 |
| 9,833,323 | B2 * | 12/2017 | Richter | A61F 2/3868 |
| 9,867,708 | B2 * | 1/2018 | Donno | A61F 2/3859 |
| 2002/0010512 | A1 * | 1/2002 | Takei | A61F 2/3886 623/20.31 |
| 2005/0096747 | A1 | 5/2005 | Tuttle et al. | |
| 2007/0135926 | A1 * | 6/2007 | Walker | A61F 2/3859 623/20.31 |
| 2011/0071802 | A1 * | 3/2011 | Bojarski | A61F 2/30942 703/1 |
| 2011/0153026 | A1 * | 6/2011 | Heggendorn | A61F 2/3859 623/20.35 |
| 2012/0323336 | A1 * | 12/2012 | Parisi | A61F 2/3859 623/20.35 |
| 2013/0226305 | A1 * | 8/2013 | Donno | A61F 2/3859 623/20.35 |
| 2013/0297032 | A1 * | 11/2013 | Li | A61F 2/3859 623/20.35 |
| 2014/0330388 | A1 * | 11/2014 | Mizuguchi | A61F 2/38 623/20.21 |
| 2016/0270858 | A1 * | 9/2016 | Park | A61B 34/10 |
| 2017/0266013 | A1 * | 9/2017 | Enomoto | A61F 2/3868 |
| 2018/0036128 | A1 * | 2/2018 | Leung | A61F 2/30942 |

FOREIGN PATENT DOCUMENTS

| | | |
|---|---|---|
| JP | 2013-138709 A | 7/2013 |
| JP | 2013-215456 A | 10/2013 |

* cited by examiner

FIG. 1
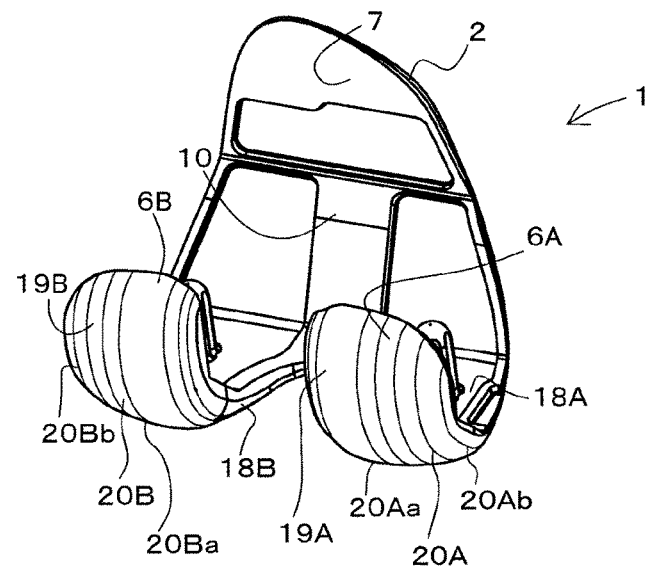
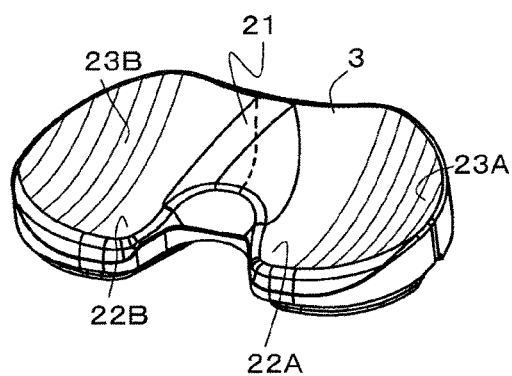

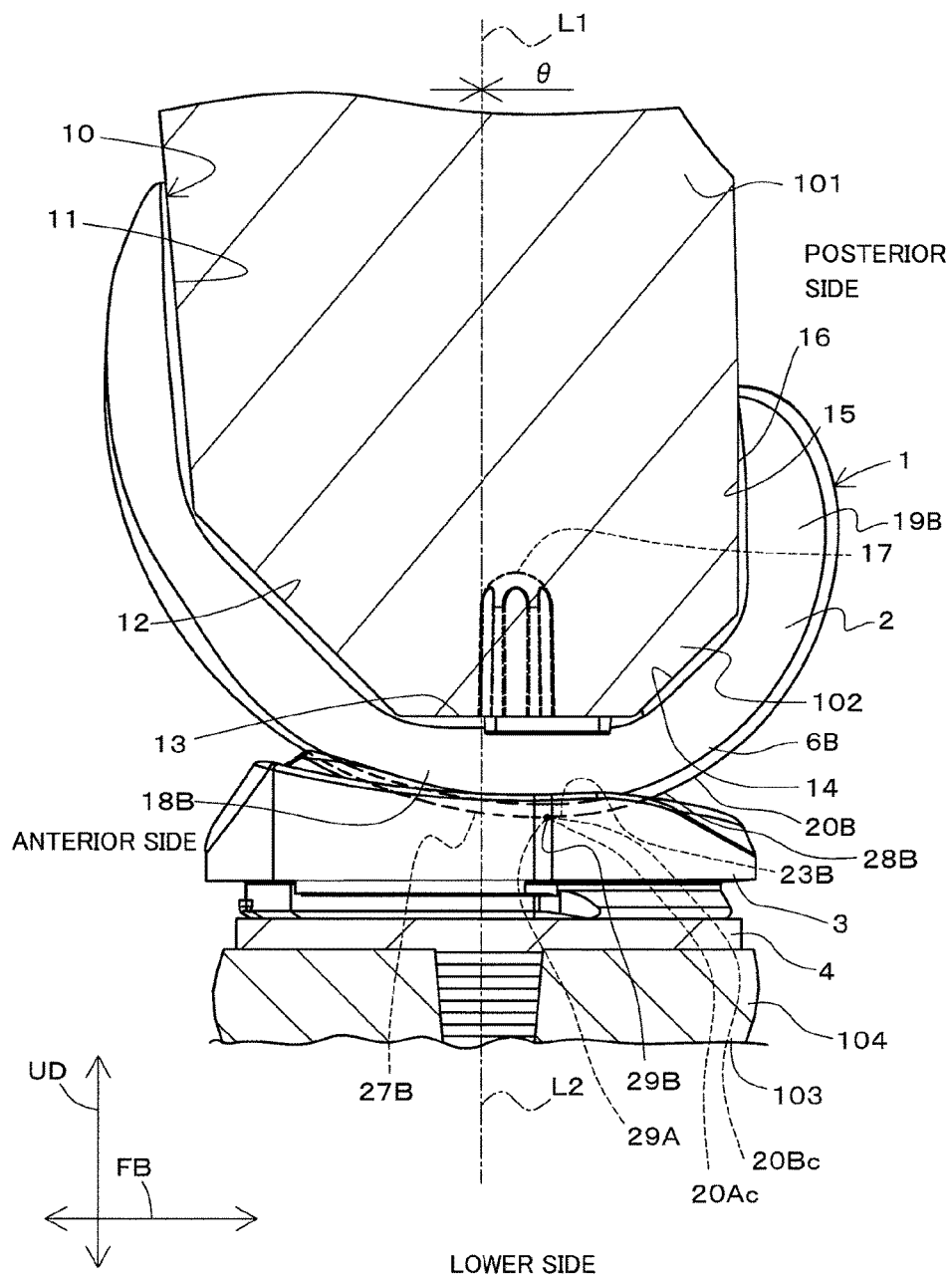

ARTIFICIAL KNEE JOINT IMPLANT

TECHNICAL FIELD

The present invention relates to artificial knee joint implants to be used in surgery to replace a knee joint of a patient with an artificial knee joint.

BACKGROUND ART

Commonly, an artificial knee joint has a femur component that is to be fixed to a distal portion of a femur, and a tibia component that is to be fixed to a proximal portion of a tibia (e.g. see Patent Document 1). The femur component includes an arc-shaped femur sliding face. The femur sliding face can come into contact with a tibia sliding face, which is formed in the tibia component. The tibia sliding face is a concavely curved face that is recessed toward the tibia side. Bending motion of the knee is performed as a result of the femur sliding face sliding with respect to the tibia sliding face.

CITATION LIST

Patent Document

Patent Document 1: JP 2013-215456A

DISCLOSURE OF THE INVENTION

Problem to be Solved by the Invention

Usually, a normal knee in a human body and a femur component are formed such that the curvature radius of a condylar portion at the distal end is large when a patient is viewed from the side, and is also formed such that the curvature radius of a posterior condylar portion is small. The curvature radius of a concavely curved face in the tibia sliding face is fixed, and is set to be large so as to fit the shape of the condylar portion at the distal end having a large curvature radius.

As a result of having such a configuration, when the bending angle of the patient's knee is small (when the patient is near to assuming an upright posture), the portion of the femur component with a large curvature radius comes into contact with the tibia sliding face. Accordingly, if the bending angle is small, the contact area between the femur component and the tibia component is large, and the constraint force of the femur component and the tibia component in the anterior-posterior direction and the left-right direction of the patient (hereinafter referred to simply as "constraint force") is large. On the contrary, when the bending angle is large (when the patient has assumed a bent-knee posture), the portion of the femur component with a small curvature radius comes into contact with the tibia sliding face. For this reason, the contact area between the femur component and the tibia component is small, and the aforementioned constraint force is small.

Regarding an allowable degree of medial pivot motion of the femur and the tibia component, the larger the curvature radius of the component is, the higher the allowable degree is. The smaller the curvature radius of the component is, the lower the allowable degree is. As mentioned above, the larger the bending angle is, the higher the allowable degree is.

As a configuration for changing such a relationship between the constraint force and medial pivot motion, it is conceivable to change the curvature radii of the femur sliding face and the tibia sliding face. For example, it is conceivable to further flatten the tibia sliding face by setting a larger curvature radius for the tibia sliding face (employ a flat-type tibia sliding face). The flat-type tibia sliding face receives the femur sliding face with a portion having a substantially flat face. In this case, the allowable degree of medial pivot motion is high, but the constraint force is weak.

On the other hand, it is conceivable to set a smaller curvature radius for the tibia sliding face (employ a curved-type tibia sliding face). In this case, the tibia sliding face has a curved shape with a deeper recess. This curved-type tibia sliding face receives the femur sliding face with two curved portions with deep recesses provided on the medial side and the lateral side. In this case, the constraint force is large, but the allowable degree of medial pivot motion is low.

Thus, with the conventional configuration, it is difficult to realize a configuration that increases the allowable degree of medial pivot motion while ensuring the constraint force regardless of the bending angle.

In view of the foregoing situation, the present invention aims to enable, in an artificial knee joint implant, the constraint force of a femur component and a tibia component in the anterior-posterior direction and the left-right direction of a patient to be increased, and to enable the allowable degree of medial pivot motion to be increased, regardless of the bending angle.

Means for Solving the Problem (1) An artificial knee joint implant according to the present invention for achieving the above-stated object is an artificial knee joint implant including: a femur component to be fixed to a distal portion of a femur of a patient; and a tibia component to be fixed to a proximal portion of a tibia of the patient, wherein the femur component includes a convex femur sliding face, the tibia component has a concave tibia sliding face and is to face the femur sliding face, and the femur sliding face and the tibia sliding face each include a variable region in which a curvature radius varies in a predetermined direction.

With this configuration, the contact state between the sliding faces of the femur component and the tibia component can be varied in accordance with the bending angle of the patient's knee. As a result, the constraint force of the femur component and the tibia component in the anterior-posterior direction and the left-right direction of the patient can be increased, and the allowable degree of medial pivot motion of the patient can be increased, regardless of the bending angle. As a result, an artificial knee joint implant capable of increasing the constraint force of the femur component and the tibia component in the anterior-posterior direction and the left-right direction of the patient, and increasing the allowable degree of medial pivot motion can be realized. In addition, when the knee is in a state of deep flexion, medial pivot motion and rearward movement can be further promoted on the lateral side than on the medial side with an increase in the bending angle.

(2) Preferably, the predetermined direction includes a medial-lateral direction along to a left-light direction of the patient, and in the variable region, the curvature radius in a cross-section perpendicular to the medial-lateral direction varies in the medial-lateral direction.

With this configuration, regardless of the bending angle, the constraint force of the femur sliding face and the tibia sliding face can be increased, and the allowable degree of medial pivot motion of the femur sliding face and the tibia sliding face can be increased with a simple configuration in which the curvature radii of the femur sliding face and the tibia sliding face are varied in the medial-lateral direction.

(3) More preferably, in at least a part of the tibia sliding face, the curvature radius of the tibia sliding face decreases toward a component end side from a bottom portion of the tibia sliding face in the medial-lateral direction.

With this configuration, when the bending angle of the patient's knee is relatively small, the femur sliding face can come into contact with a front part of the tibia sliding face and a most part of the tibia sliding face on the component end side. Accordingly, a large constraint force can be secured. When the bending angle is relatively large, the femur sliding face is received by a portion of the tibia sliding face with a small curvature radius on the component end side. Thus, a large constraint force can be secured. That is to say, the femur sliding face is held with a large constraint force by the tibia sliding face regardless of the bending angle. In addition, a large curvature radius of the bottom portion of the component and a small curvature radius on the component end side can further increase the allowable degree of medial pivot motion regardless of the bending angle.

(4) More preferably, in the tibia sliding face, the curvature radius between the bottom portion of the tibia sliding face in the medial-lateral direction and a position corresponding to 5% of an overall length of the tibia sliding face in a component medial-lateral direction from the component end side is set to vary by 15% or more.

This configuration can exhibit a significant effect of synergistically increasing both the allowable degree of medial pivot motion and the constraint force by setting the relationship regarding the curvature radius of the tibia sliding face as described above.

(5) Preferably, the predetermined direction includes an anterior-posterior direction of the patient, and in the variable region, the curvature radius varies in the anterior-posterior direction.

With this configuration, the contact state between the femur sliding face and the tibia sliding face can be varied in accordance with a change in the bending angle. As a result, regardless of the bending angle, the constraint force can be increased, and the allowable degree of medial pivot motion can also be increased.

(6) More preferably, the femur component includes a distal-end condylar portion to be attached to a distal end of the femur, and a posterior condylar portion arranged rearward of the distal-end condylar portion, the femur sliding face is formed so as to span both the distal-end condylar portion and the posterior condylar portion, and in a cross-section perpendicular to a medial-lateral direction along to a left-right direction of the patient, the curvature radius of the femur sliding face in the distal-end condylar portion is set to be larger than the curvature radius of the femur sliding face in the posterior condylar portion.

This configuration can make the shape of the femur sliding face more similar to the shape of a normal knee in a human body.

(7) Preferably, the predetermined direction includes a medial-lateral direction along to a left-light direction of the patient, and in at least a part of the femur sliding face, the curvature radius of the femur sliding face in a cross-section perpendicular to the medial-lateral direction decreases toward a component end side from a bottom portion of the femur sliding face in the medial-lateral direction.

With this configuration, when the knee is bent, the femur sliding face in the posterior condylar portion is received on the component end side in the tibia sliding face. As a result, it is possible to avoid impingement between the femur component and the tibia component due to medial pivot motion, while suppressing a decrease in the constraint force. Accordingly, a decrease in the constraint force can be suppressed, and the allowable degree of medial pivot motion can be further increased.

(8) More preferably, the femur component includes a distal-end condylar portion to be attached to a distal end of the femur, and a posterior condylar portion arranged rearward of the distal-end condylar portion, the femur sliding face is formed so as to span both the distal-end condylar portion and the posterior condylar portion, in the femur sliding face in the distal-end condylar portion, the curvature radius between the bottom portion of the femur sliding face in the medial-lateral direction and a position corresponding to 5% of an overall length of the femur sliding face in a component medial-lateral direction from the component end side is set to vary by 45% or more, and in the femur sliding face in the posterior condylar portion, the curvature radius between the bottom portion of the femur sliding face in the medial-lateral direction and a position corresponding to 5% of an overall length of the femur sliding face in the component medial-lateral direction from the component end side is set to vary by 5% or more.

With this configuration, by setting the relationship regarding the curvature radii of the respective parts of the femur sliding face as described above, a significant effect of synergistically increasing both the allowable degree of medial pivot motion and the constraint force can be exhibited.

(9) Preferably, the femur component includes a distal-end condylar portion to be attached to a distal end of the femur, and a posterior condylar portion arranged rearward of the distal-end condylar portion, and a pair of the posterior condylar portions are arranged side-by-side in a medial-lateral direction along to a left-right direction of the patient, and when curvature radii of shoulder portions of a distal part and a proximal part on the component end side of the posterior condylar portion located on a lateral side in the medial-lateral direction are r1 and r2, respectively, r2 is set to be larger than r1 when the femur component is viewed from the back.

With this configuration, when the bending angle of the knee is large (when the knee is in a state of deep flexion), the portion of the femur sliding face that comes into contact with the tibia sliding face is changed, with an increase in the bending angle, from the portion where the curvature radius is set to r1 to the portion where the curvature radius is set to r2. Thus, the femur sliding face and the tibia sliding face can be brought into contact with each other so as to further promote medial pivot motion and rearward movement. As a result, with an increase in the bending angle when the knee is in a state of deep flexion, the allowable degree of medial pivot motion can be further increased, and rearward movement can be promoted.

(10) More preferably, when curvature radii of shoulder portions of a distal part and a proximal part on the component end side of a posterior condylar portion located on a medial side in the medial-lateral direction are r3 and r4, respectively, r4 is set to be larger than r3 when the femur component is viewed from the back.

With this configuration, when the knee is in a state of deep flexion, the portion of the femur sliding face that comes into contact with the tibia sliding face changes, with an increase in the bending angle, from the portion where the curvature radius is set to r3 to the portion where the curvature radius is set to r4. Thus, the femur sliding face and the tibia sliding face can be brought into contact with each other so as to further promote medial pivot motion and rearward movement. As a result, with an increase in the bending angle when the knee is in a state of deep flexion, the allowable degree of medial pivot motion can be further increased, and rearward movement can be promoted.

(11) More preferably, r2 is set to be larger than r4.

With this configuration, when the knee is in a state of deep flexion, the femur sliding face and the tibia sliding face can be brought into contact with each other so as to further promote medial pivot motion with an increase in the bending angle. As a result, the allowable degree of medial pivot motion can be further increased on the lateral side than on the medial side.

(12) Preferably, the femur component has a front part that faces forward when the patient has assumed an upright posture, and in the front part, on a component end side, the curvature radius of a portion extending in a medial-lateral direction of the patient varies so as to decrease continuously or stepwise toward a proximal side of the femur.

With this configuration, the shape of the front part of the femur component on the component end side can be curved to a greater degree. It is thus possible, when the patient has assumed an upright posture, to avoid the front part of the femur component on the component end side interfering with the concave tibia sliding face of the tibia component. As a result, when the patient has assumed an upright posture, an appropriate positional relationship can be maintained without the femur component interfering with the tibia component.

Effects of the Invention

According to the present invention, in an artificial knee joint implant, the constraint force of a femur component and a tibia component in the anterior-posterior direction and the left-right direction of a patient can be increased, and the allowable degree of medial pivot motion can be increased, regardless of the bending angle. In addition, when the knee is in a state of deep flexion, medial pivot motion and rearward movement can be further promoted on the lateral side than on the medial side with an increase in the bending angle.

BRIEF DESCRIPTION OF THE DRAWINGS

FIG. 1 is a perspective view of an artificial knee joint implant according to an embodiment of the present invention.

FIG. 2 is a partial cross-sectional view showing a state where a femur component is fixed to a distal portion of a femur of a patient, and a tibia component is fixed to a proximal portion of a tibia of the patient, when viewed from the side of the patient.

FIG. 10(A) shows a state where the bending angle θ is zero degrees. FIG. 10(B) shows a state where the bending angle θ is 90 degrees. FIG. 10(C) shows a state in a range of the bending angle θ from 90 degrees to the maximum bending angle.

FIG. 11(A) shows sliding face regions that constrain anterior-posterior and leftward-rightward motion of the femur sliding face when the bending angle is zero degrees (when an upright posture is assumed). FIG. 11(B) shows sliding face regions that constrain anterior-posterior and leftward-rightward motion of the femur sliding faces when the bending angle has increased from zero degrees (when the knee is in a bent posture).

DESCRIPTION OF EMBODIMENTS

Hereinafter, a mode for carrying out the present invention will be described with reference to the drawings. The present invention can be widely applied as an artificial knee joint implant to be used in surgery to replace a knee joint with an artificial knee joint.

FIG. 1 is a perspective view of an artificial knee joint implant 1 according to an embodiment of the present invention. The artificial knee joint implant 1 is used in surgery to replace a knee joint of a patient with an artificial knee joint. For example, the artificial knee joint implant 1 is used to recover normal functions of a knee of a patient whose knee joint has become highly deformed due to gonarthrosis, chronic articular rheumatism, or the like.

The artificial knee joint implant 1 has a femur component 2 and a tibia component 3.

Figure 3A:
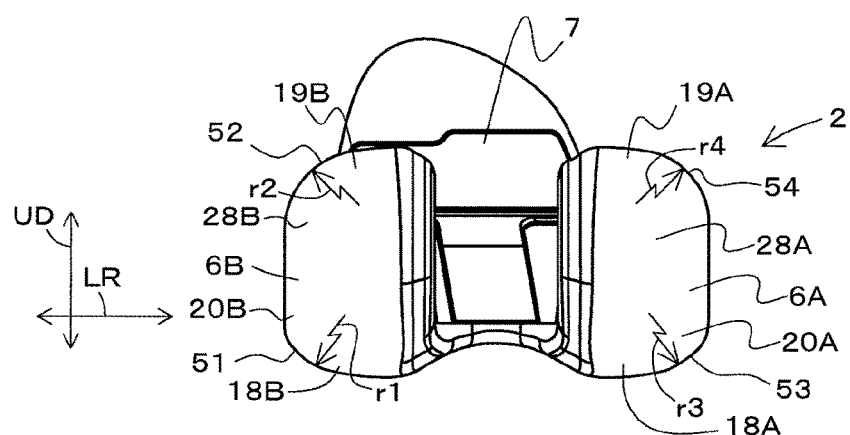
FIG. 3(A) is a back view of the femur component.
Figure 3B:
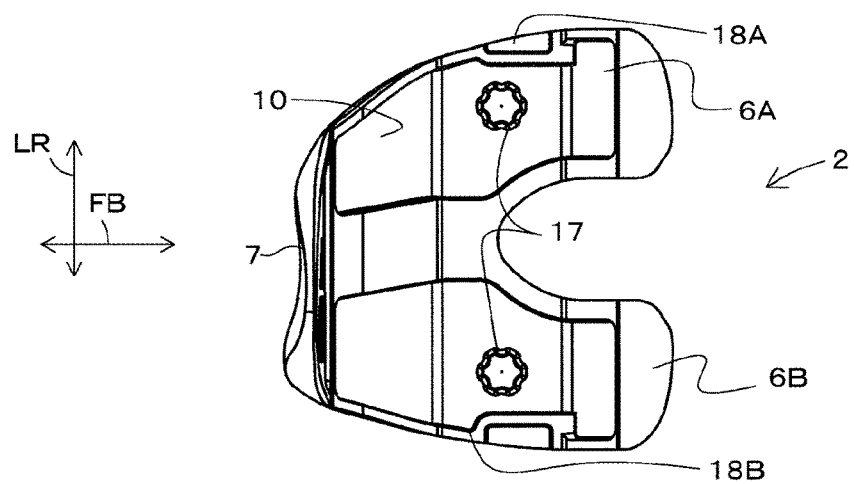
FIG. 3(B) is a plan view of the femur component.
Figure 3C:
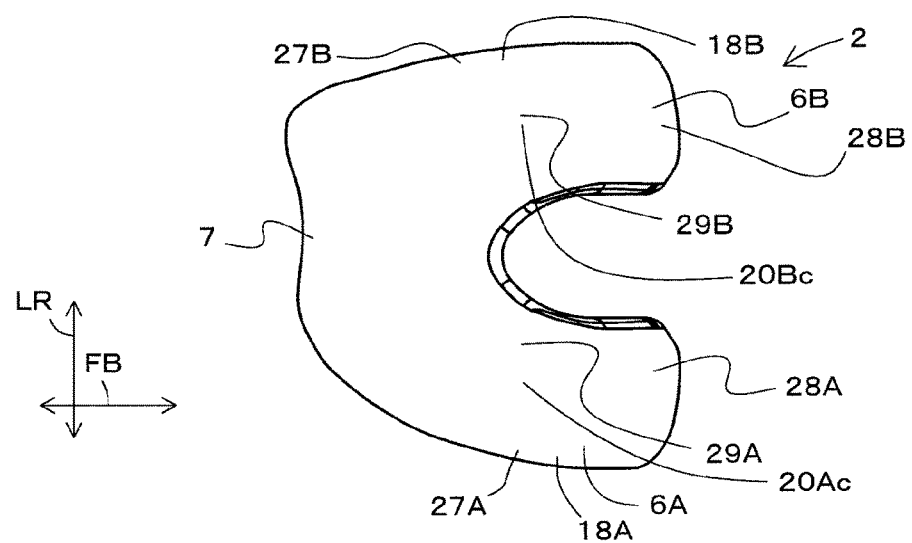
FIG. 3(C) is a bottom portion view of the femur component.

FIG. 2 is a partial cross-sectional view showing a state where the femur component 2 is fixed to a distal portion 102 of a femur 101 of a patient, and the tibia component 3 is fixed to a proximal portion 104 of a tibia 103 of the patient, when viewed from the side of the patient. FIG. 3(A) is a back view of the femur component 2. FIG. 3(B) is a plan view of the femur component 2. FIG. 3(C) is a bottom portion view of the femur component 2.

Referring to FIGS. 1 and 2, the femur component 2 is fixed to the distal portion 102 of the femur 101. The tibia component 3 is fixed to the proximal portion 104 of the tibia 103 via a tibia tray 4. The femur component 2 and the tibia component 3 are relatively displaced due to a bending motion of the patient's knee. This relative displacement is achieved as a result of the femur component 2 and the tibia component 3 coming into rolling contact and/or sliding contact with each other. This relative displacement varies the bending angle θ of the patient's knee.

The bending angle θ is the angle formed by an axis L1 of the distal portion 102 of the femur 101 and an axis L2 of the proximal portion 104 of the tibia 103. Usually, the bending angle θ is set so as to vary in a range from zero degrees to a hundred and several tens of degrees, for example.

In the following description, "component end side" and "component central side" refer respectively to the end side and the central side in the components in the medial-lateral direction LR of the patient in which the femur component 2 and the tibia component 3 are installed.

"Front/anterior" and "rear/posterior" refer respectively to the front and the back of the patient. "Upper/above" and "lower/below" refer respectively to the upper side and the lower side of the patient. Hereinafter, the artificial knee joint implant 1 will be described based on a reference state, which is a state where the bending angle θ is zero, i.e. a state where the patient is standing straight, unless stated otherwise. This embodiment will describe a state where the artificial knee joint implant 1 is attached to the left leg of the patient.

Referring to FIGS. 1, 2, and 3(A) to 3(C), the femur component 2 is made of a biocompatible material, for example. The femur component 2 is formed in a U shape when viewed from the side.

The femur component 2 includes a medial condyle 6A and an lateral condyle 6B.

The medial condyle 6A and the lateral condyle 6B are arranged side-by-side in the left-right direction. The medial condyle 6A and the lateral condyle 6B are formed in a shape extending from the front of the distal portion 102 of the femur 101 to the rear of the distal portion 102. The front part of the medial condyle 6A and the front part of the lateral condyle 6B are connected to each other by a connecting portion 7.

The medial condyle 6A and the lateral condyle 6B each have an inner face that faces toward the distal portion 102 of the femur 101. These inner faces are fixed to the distal portion 102 of the femur 101. Specifically, a femur fixing portion 10 is formed in each of the medial condyle 6A and the lateral condyle 6B. The femur fixing portions 10 each have a first fixing portion 11, a second fixing portion 12, a third fixing portion 13, a fourth fixing portion 14, and a fifth fixing portion 15. A cut-bone face 16 is formed on the distal portion 102 of the femur 101. This cut-bone face 16 is formed by a surgeon using a bone-cutting tool to cut a part of the distal portion 102, for example, and has a shape that fits the shapes of the first fixing portion 11 to the fifth fixing portion 15.

The first fixing portion 11 faces rearward, and extends obliquely downward to the rear side. The first fixing portion 11 is fixed to a portion of the cut-bone face 16 that faces forward. The second fixing portion 12 extends obliquely downward to the rear side from a lower end of the first fixing portion 11. The second fixing portion 12 faces obliquely upward to the rear side. The second fixing portion 12 is fixed to a portion of the cut-bone face 16 that faces obliquely downward to the front side.

The third fixing portion 13 extends substantially horizontally and rearward from a lower end of the second fixing portion 12. The third fixing portion 13 faces upward, and is fixed to a portion of the cut-bone face 16 that faces downward. The fourth fixing portion 14 extends obliquely upward to the rear side from a rear end of the third fixing portion 13. The fourth fixing portion 14 faces obliquely upward to the front side, and is fixed to a portion of the cut-bone face 16 that faces obliquely downward to the rear side. The fifth fixing portion 15 extends upward from an upper end of the fourth fixing portion 14. The fifth fixing portion 15 faces forward, and is fixed to a portion of the cut-bone face 16 that faces rearward. The respective fixing portions 11 to 15 and the cut-bone face 16 are fixed to each other using bone cement, a coating agent that contains a bioactive material, or the like.

A projecting portion 17 is formed in each third fixing portion 13. The projecting portions 17 are passed through a pair of recessed portions formed in the cut-bone face 16 of the distal portion 102, and are fixed to these recessed portions.

Outer faces of the medial condyle 6A and the lateral condyle 6B each include convex femur sliding faces 20A and 20B. The femur sliding faces 20A and 20B are provided as curved faces that slide against later-described tibia sliding faces 23A and 23B of the tibia component 3 with bending motion of the patient's knee.

The femur sliding faces 20A and 20B are each formed in a convexly curved shape that faces outward of the femur component 2. The femur sliding faces 20A and 20B each have a portion adjacent to the third fixing portion 13, a portion adjacent to the fourth fixing portion 14, and a portion adjacent to the fifth fixing portion 15. Thus, the femur sliding faces 20A and 20B surround a part of the distal portion 102 when viewed from the side.

The femur sliding face 20A is formed so as to span both a distal-end condylar portion 18A and a posterior condylar portion 19A that are provided in the medial condyle 6A. Similarly, the femur sliding face 20B is formed so as to span both a distal-end condylar portion 18B and a posterior condylar portion 19B that are provided in the lateral condyle 6B.

The pair of distal-end condylar portions 18A and 18B face the distal portion 102 of the femur 101 in the up-down direction UD, and are arranged side-by-side in the medial-lateral direction LR. The posterior condylar portions 19A and 19B are arranged rearward of the corresponding distal-end condylar portions 18A and 18B. The pair of posterior condylar portions 19A and 19B are arranged side-by-side in the medial-lateral direction LR.

The distal-end condylar portions 18A and 18B are arranged so as to oppose a lower face of the cut-bone face 16 of the distal portion 102 of the femur 101, and are attached to the distal end of this distal portion 102. The posterior condylar portions 19A and 19B are provided as portions that extend obliquely upward to the rear side from the distal-end condylar portions 18A and 18B. The posterior condylar portions 19A and 19B constitute the fourth fixing portion 14 and a part of the fifth fixing portion 15, and are arranged rearward of the femur fixing portions 10.

The femur component 2 having the above-described configuration is slidably supported by the tibia component 3.

The tibia component 3 is supported by the tibia tray 4, and is fixed to the proximal portion 104 of the tibia 103 via the tibia tray 4. The tibia tray 4 and the proximal portion 104 are fixed to each other using bone cement, a coating agent that contains a bioactive material, or the like. The tibia component 3 is fixed to an upper face of the tibia tray 4.

The tibia component 3 is a flat, plate-shaped member that is made of a synthetic resin or the like. The tibia component 3 is formed in a disk-like shape that is elongated in the left-right direction.

The tibia component 3 has an intermediate portion 21, a medial fossa 22A, and an lateral fossa 22B.

The intermediate portion 21 is located between the medial fossa 22A and the lateral fossa 22B in the left-right direction (medial-lateral direction LR) of the patient. This intermediate portion 21 is provided as a portion that partitions the medial fossa 22A and the lateral fossa 22B from each other, and is configured not to come into contact with the femur component 2. The medial fossa 22A is arranged inward of the intermediate portion 21 in the medial-lateral direction LR. The lateral fossa 22B is arranged outward of the intermediate portion 21 in the medial-lateral direction LR.

The medial fossa 22A and the lateral fossa 22B are provided as recessed parts arranged so as to face the medial condyle 6A and the lateral condyle 6B, respectively, of the femur component 2.

A concave tibia sliding face 23A is formed in a face of the medial fossa 22A that opposes the medial condyle 6A of the femur component 2. Similarly, a concave tibia sliding face 23B is formed in a face of the lateral fossa 22B that opposes the lateral condyle 6B of the femur component 2. These two tibia sliding faces 23A and 23B are each formed in a shape that is recessed toward the proximal portion 104 of the tibia 103.

The tibia sliding face 23A of the medial fossa 22A faces the femur sliding face 20A of the medial condyle 6A, and is in slidable contact with the femur sliding face 20A. The tibia sliding face 23B of the lateral fossa 22B faces the femur sliding face 20B of the lateral condyle 6B, and is in slidable contact with the femur sliding face 20B. Note that the tibia sliding face 23A of the medial fossa 22A and the tibia sliding face 23B of the lateral fossa 22B form a symmetrical shape in the medial-lateral direction LR.

Figure 4:
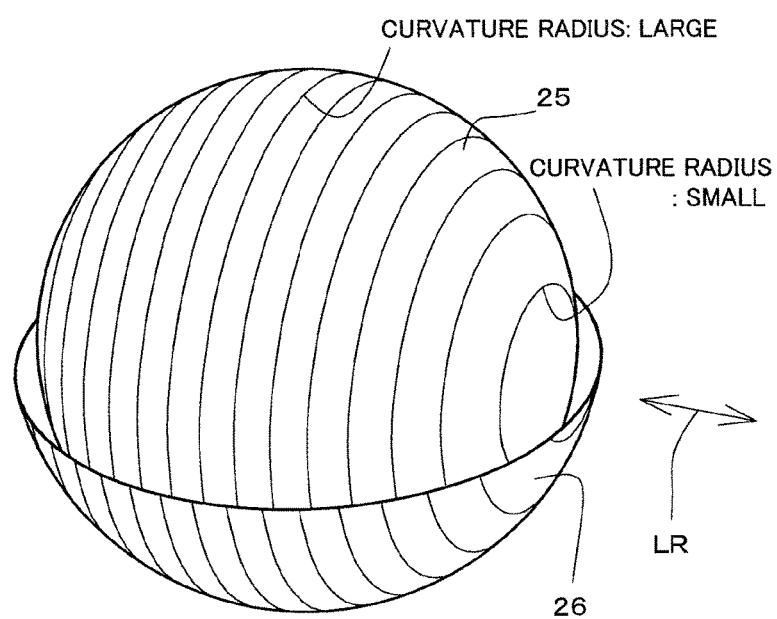
FIG. 4 is a conceptual diagram for illustrating a configuration of a femur sliding face and a tibia sliding face.
Figure 5A:
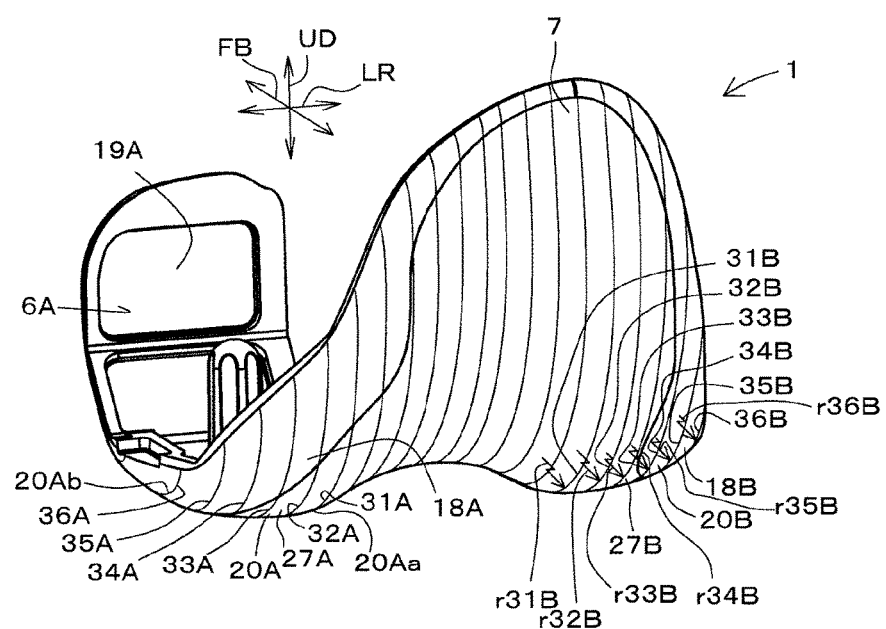
FIGS. 5(A) and 5(B) are perspective views of the femur component when viewed from the front, with auxiliary lines for illustrating the curvature radii of femur sliding faces added.
Figure 5B:
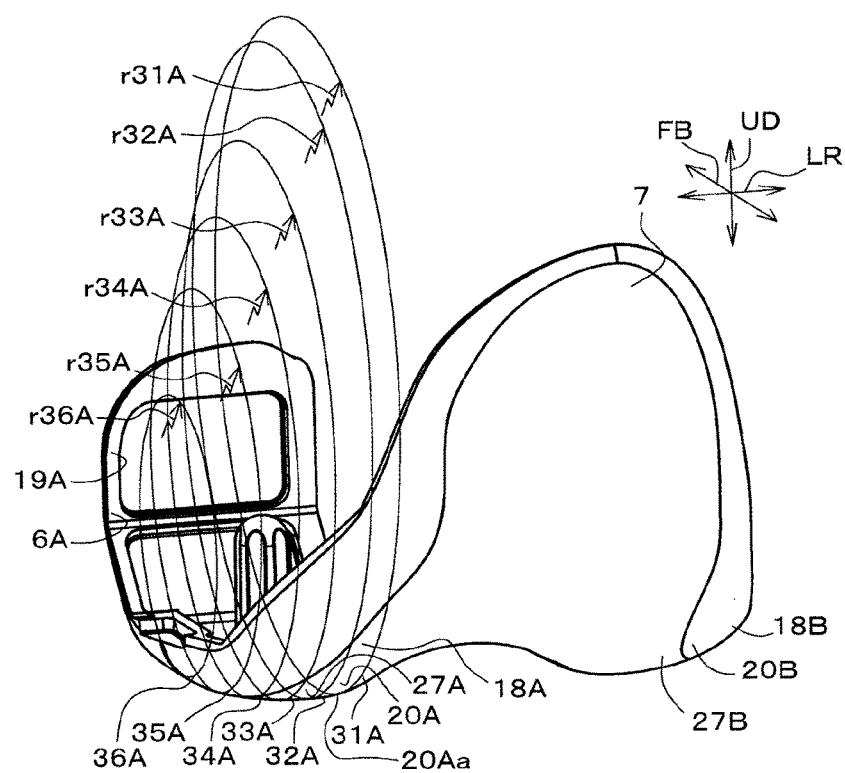

Next, the femur sliding faces 20A and 20B will be described in more detail. FIG. 4 is a conceptual diagram for illustrating a configuration of the femur sliding faces 20A and 20B and the tibia sliding faces 23A and 23B. FIGS. 5(A) and 5(B) are perspective views of the femur component 2 as viewed from the front, with auxiliary lines for illustrating the curvature radii of the femur sliding faces 20A and 20B added.

Figure 6A:
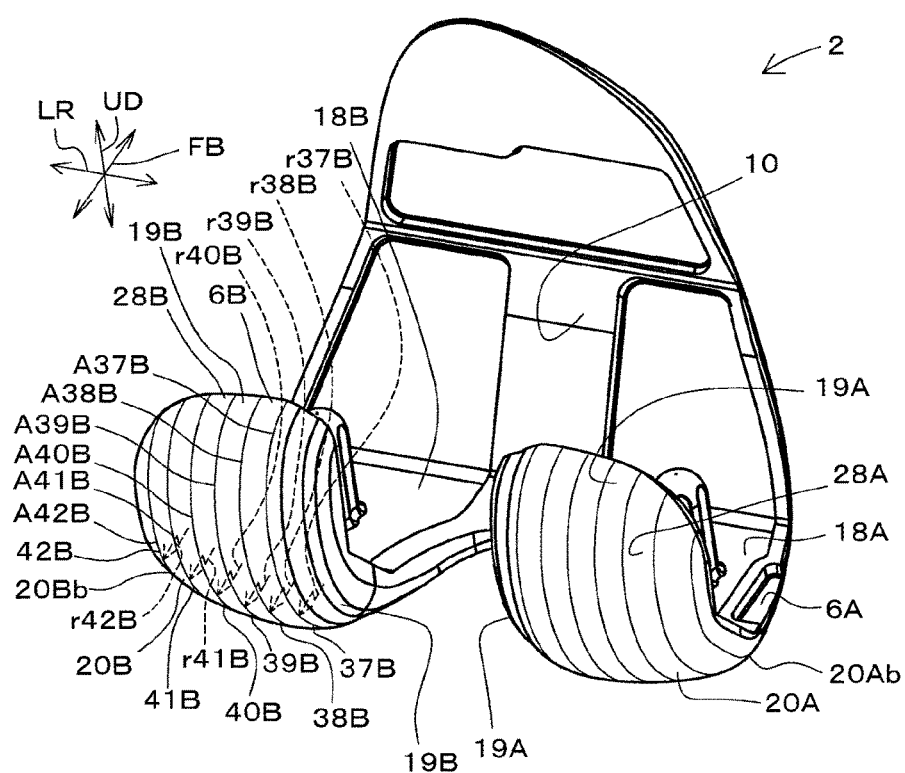
FIGS. 6(A) and 6(B) are perspective views of the femur component when viewed from the back, with auxiliary lines for illustrating the curvature radii of the femur sliding faces added.
Figure 6B:
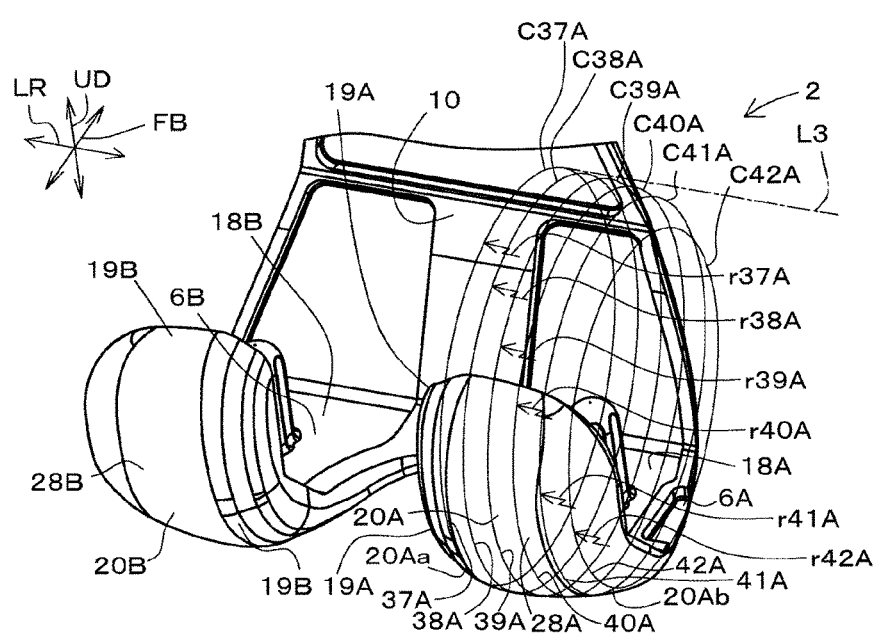

FIGS. 6(A) and 6(B) are perspective views of the femur component 2 as viewed from the back, with auxiliary lines for illustrating the curvature radii of the femur sliding faces 20A and 20B added.

FIG. 4 shows a sphere 25 for illustrating an image of the femur sliding faces 20A and 20B, and a hemisphere 26 for illustrating an image of the tibia sliding faces 23A and 23B. The curvature radius of the sphere 25 is smaller than the curvature radius of the hemisphere 26 in the diagram. In the sphere 25 and the hemisphere 26, the curvature radius of a circle in a cross-section perpendicular to the medial-lateral direction LR decreases toward the end sides from the central side in the medial-lateral direction LR.

Referring to FIGS. 1, 4, 5(A), 5(B), 6(A), and 6(B), in this embodiment, the femur sliding faces 20A and 20B and the corresponding tibia sliding faces 23A and 23B are formed based on an idea that spherical portions come into contact with each other. The femur sliding faces 20A and 20B are formed closer to the component end of the medial condyle 6A and lateral condyle 6B, respectively.

In this embodiment, first ends 20Aa and 20Ba of the femur sliding faces 20A and 20B are provided on the distal end side in the corresponding medial condyle 6A and the lateral condyle 6B, respectively, in the medial-lateral direction LR. Also, in this embodiment, second ends 20Ab and 20Bb of the femur sliding faces 20A and 20B are provided on the component end side in the corresponding medial condyle 6A and the lateral condyle 6B, respectively, in the medial-lateral direction LR.

The femur sliding faces 20A and 20B are formed as variable regions in which the curvature radii of the femur sliding faces 20A and 20B in cross-sections perpendicular to the medial-lateral direction LR vary in the medial-lateral direction LR, which serves as a predetermined direction. The femur sliding faces 20A and 20B are also formed as variable regions in which the curvature radii of the femur sliding faces 20A and 20B in cross-sections perpendicular to the anterior-posterior direction FB vary in the anterior-posterior direction FB, which serves as a predetermined direction.

In this embodiment, the femur sliding faces 20A and 20B are formed as regions in which the curvature radii of the femur sliding faces 20A and 20B in cross-sections perpendicular to the medial-lateral direction LR decrease toward the component end side from bottom portions 20Ac and 20Bc of the femur sliding faces 20A and 20B in the medial-lateral direction LR.

The femur sliding face 20A has a first part 27A provided in the distal-end condylar portion 18A, and a second part 28A provided in the posterior condylar portion 19A.

The first part 27A and the second part 28A (see FIG. 3(C)) are parts that extend in the anterior-posterior direction FB. The first part 27A is a curved part arranged forward of the second part 28A, and has a different curvature radius from the curvature radius of the second part 28A. In this embodiment, a boundary portion 29A between the first part 27A and the second part 28A is a part where the femur sliding face 20A is in contact with the tibia sliding face 23A when the bending angle θ is zero degrees. That is to say, the boundary portion 29A is the rear end of the distal-end condylar portion 18A, and is the front end of the posterior condylar portion 19A.

The curvature radii of the first part 27A and the second part 28A in a cross-section perpendicular to the medial-lateral direction LR vary in the medial-lateral direction LR, which serves as a predetermined direction. Note that the medial-lateral direction LR corresponds to the left-right direction of the patient.

The first part 27A will now be described in more detail. The first part 27A is formed in a shape corresponding to a shape that includes a part of the sphere 25. A plurality of (at least six in this embodiment) curvature radii are set for the first part 27A. Specifically, in this embodiment, the first part 27A of the femur sliding face 20A has a first curvature radius portion 31A, a second curvature radius portion 32A, a third curvature radius portion 33A, a fourth curvature radius portion 34A, a fifth curvature radius portion 35A, and a sixth curvature radius portion 36A, as shown clearly in FIGS. 5(A) and 5(B).

The first to sixth curvature radius portions 31A to 36A are arranged at substantially equal intervals in the medial-lateral direction LR. The first curvature radius portion 31 is arranged on the first end 20Aa side in the femur sliding face 20A. The sixth curvature radius portion 36 is arranged on the second end 20Ab side in the femur sliding face 20A.

The curvature radius of the first curvature radius portion 31A (first curvature radius r31A) is set to be approximately 80% (82% in this embodiment) of a reference curvature radius (reference curvature radius rb). As will be described later, the reference curvature radius rb is the curvature radius of bottom portion 23Ac/23Bc of the tibia sliding face 23A (23B) in FIG. 9 in a cross-section perpendicular to the medial-lateral direction LR as viewed from the side. The curvature radius of the second curvature radius portion 32A (second curvature radius r32A) is set to be approximately 80% (79% in this embodiment) of the reference curvature radius rb. The curvature radius of the third curvature radius portion 33A (third curvature radius r33A) is set to be approximately 70% (67% in this embodiment) of the reference curvature radius rb.

The curvature radius of the fourth curvature radius portion 34A (fourth curvature radius r34A) is set to be approximately 60% (57% in this embodiment) of the reference curvature radius rb. The curvature radius of the fifth curvature radius portion 35A (fifth curvature radius r35A) is set to be approximately 50% (49% in this embodiment) of the reference curvature radius rb. The curvature radius of the sixth curvature radius portion 36A (sixth curvature radius r36A) is set to be approximately 30% (34% in this embodiment) of the reference curvature radius rb. In the femur sliding face 20A, portions between adjacent curvature radius portions in the first to sixth curvature radius portions 31A to 36A are formed as smooth faces. Thus, the entire femur sliding face 20A is formed as a smoothly curved face.

In the first part 27A of the femur sliding face 20A, the sixth curvature radius r36A of the sixth curvature radius portion 36A that is closest to the component end side in the medial-lateral direction LR among the first to sixth curvature radius portions 31A to 36A, is set to 45% or less of the first curvature radius r31A of the first curvature radius portion 31A that is closest to the component central side in the medial-lateral direction LR among the first to sixth curvature radius portions 36. In this embodiment, in the first part 27A, the curvature radius between the bottom portion 20Ac of the femur sliding face 20A in the medial-lateral direction LR and a position corresponding to 5% of the overall length of the femur sliding face 20A in the component medial-lateral direction LR from the component end side is set to vary by 45% or more. Note that the bottom portion 20Ac is also the distal end of the second curvature radius portion 32A. In this embodiment, the sixth curvature radius r36A is set to be approximately 41% of the first curvature radius r31A. Thus, in a cross-section perpendicular to the medial-lateral direction LR, the curvature radius of the first part 27A of the femur sliding face 20A decreases from the component central side toward the component end side in the medial-lateral direction LR, and approaches the curvature radius of the second part 28A.

Next, the second part 28A of the femur component 2 will be described in more detail. The second part 28A is formed in a shape corresponding to a shape that includes a part of a sphere (not shown) having a smaller curvature radius than the curvature radius of the hemisphere 25 shown in FIG. 4. A plurality of (six in this embodiment) curvature radii are set for the second part 28A.

Referring to FIGS. 5(B), 6(A), and 6(B), in this embodiment, the second part 28A of the femur sliding face 20A has a seventh curvature radius portion 37A, an eighth curvature radius portion 38A, a ninth curvature radius portion 39A, a tenth curvature radius portion 40A, an eleventh curvature radius portion 41A, and a twelfth curvature radius portion 42A.

The seventh to twelfth curvature radius portions 37A to 42A are arranged at substantially equal intervals in the medial-lateral direction LR. The positions of the seventh to twelfth curvature radius portions 37A to 42A in the medial-lateral direction LR are aligned with the positions of the first to sixth curvature radius portions 31A to 36A, respectively. That is to say, the seventh curvature radius portion 37A and the first curvature radius portion 31A are arranged in a line in the anterior-posterior direction FB. The twelfth curvature radius portion 42A and the sixth curvature radius portion 36A are arranged in a line in the anterior-posterior direction FB.

In this embodiment, the curvature radii of the seventh to twelfth curvature radius portions 37A to 42A (seventh to twelfth curvature radii r37A to r42A) are set to be approximately 50% of the reference curvature radius rb. In this embodiment, the seventh curvature radius r37A is set to 53% of the reference curvature radius rb, and the eighth curvature radius r38A is set to 54% of the reference curvature radius rb. In this embodiment, the ninth curvature radius r39A is set to 53% of the reference curvature radius rb. The tenth curvature radius r40A is set to 52% of the reference curvature radius rb. The eleventh curvature radius r41A is set to 51% of the reference curvature radius rb. The twelfth curvature radius r42A is set to 47% of the reference curvature radius rb.

In the femur sliding face 20A, portions between adjacent curvature radius portions in the seventh to twelfth curvature radius portions 37A to 42A are formed as smooth faces. Thus, the entire second part 28A of the femur sliding face 20A is formed as a smoothly curved face. Furthermore, the first part 27A and the second part 28A form a smooth, continuous face, and the entirety of the femur sliding faces 20A and 20B form a continuous, smooth face.

In the second part 28A of the femur sliding face 20A, the twelfth curvature radius r42A of the twelfth curvature radius portion 42A that is closest to the component end side in the medial-lateral direction LR among the seventh to twelfth curvature radius portions 37A to 42A, is set to 95% or less of the seventh curvature radius r37A of the seventh curvature radius portion 37A that is closest to the component central side in the medial-lateral direction LR among the seventh to twelfth curvature radius portions 37A to 42A. In this embodiment, the twelfth curvature radius r42A is set to be approximately 89% of the seventh curvature radius r37A. In the second part 28A, the curvature radius between the bottom portion 20Ac in the medial-lateral direction LR and the position corresponding to 5% of the overall length of the second part 28A in the component medial-lateral direction LR from the component end side is set to vary by 5% or more. Note that the bottom portion 20Ac is also the distal end of the eighth curvature radius portion 38A. Thus, the percentage of variation in the curvature radius of the second part 28A of the femur sliding face 20A in the medial-lateral direction LR (curvature radius in a cross-section perpendicular to the medial-lateral direction LR) is set to be smaller than the percentage of variation in the curvature radius of the first part 27A of the femur sliding face 20A in the medial-lateral direction LR (the curvature radius in the aforementioned cross-section).

With the above configuration, the curvature radius in the first part 27A of the distal-end condylar portion 18A is set to be larger than the curvature radius of the second part 28A of the posterior condylar portion 19A in a portion at the same position in the medial-lateral direction LR, i.e. in a cross-section perpendicular to the medial-lateral direction LR.

Next, the femur sliding face 20B of the femur component 2 will be described with reference to FIGS. 5(A), 5(B), 6(A), and 6(B).

The femur sliding face 20B has a first part 27B provided in the distal-end condylar portion 18B, and a second part 28B provided in the posterior condylar portion 19B.

The first part 27B and the first part 27A form a substantially symmetrical shape in the medial-lateral direction LR. The second part 28B and the second part 28A form a substantially symmetrical shape in the medial-lateral direction LR. The femur sliding face 20B will now be described in more detail.

The first part 27B and the second part 28B are parts that extend in the anterior-posterior direction FB. The first part 27B is a curved part arranged forward of the second part 28B, and has a different curvature radius from the curvature radius of the second part 28B. In this embodiment, a boundary portion 29B between the first part 27B and the second part 28B (see FIG. 2) is a part where the femur sliding face 20B and the tibia sliding face 23B are in contact with each other when the bending angle θ is zero degrees. That is to say, the boundary portion 29B is the rear end of the distal-end condylar portion 18B, and is the front end of the posterior condylar portions 19B.

The curvature radii of the first part 27B and the second part 28B in a cross-section perpendicular to the medial-lateral direction LR vary in the medial-lateral direction LR, which serves as a predetermined direction. In this embodiment, the positions of the first part 27A and the first part 27B in the anterior-posterior direction FB are aligned with each other, and the positions of the second part 28A and the second part 28B in the anterior-posterior direction FB are aligned with each other.

The first part 27B of the femur component 2 will now be described in more detail. A plurality of (at least six in this embodiment) curvature radii are set for the first part 27B. More specifically, in this embodiment, the first part 27B of the femur sliding face 20B has a first curvature radius portion 31B, a second curvature radius portion 32B, a third curvature radius portion 33B, a fourth curvature radius portion 34B, a fifth curvature radius portion 35B, and a sixth curvature radius portion 36B.

In this embodiment, the curvature radius portions 31B to 36B of the femur sliding face 20B and the curvature radius portions 31A to 36A of the femur sliding face 20A are arranged symmetrically in the medial-lateral direction LR.

In this embodiment, the curvature radii of the first to sixth curvature radius portions 31B to 36B (first to sixth curvature radii r31B to r36B) in cross-sections perpendicular to the medial-lateral direction LR are set to be substantially the same as the corresponding first to sixth curvature radii r31A to r36A.

In the femur sliding face 20B, portions between adjacent curvature radius portions in the first to sixth curvature radius portions 31B to 36B are formed as smooth faces. Thus, the entire femur sliding face 20B is formed as a smoothly curved face.

Next, the second part 28B of the femur sliding face 20B will now be described in more detail. A plurality of (at least six in this embodiment) curvature radii are set for the second part 28B. More specifically, in this embodiment, the second part 28B of the femur sliding face 20B has a seventh curvature radius portion 37B, an eighth curvature radius portion 38B, a ninth curvature radius portion 39B, a tenth curvature radius portion 40B, an eleventh curvature radius portion 41B, and a twelfth curvature radius portion 42B.

The seventh to twelfth curvature radius portions 37B to 42B are arranged at substantially equal intervals in the medial-lateral direction LR. The positions of the seventh to twelfth curvature radius portions 37B to 42B in the medial-lateral direction LR are aligned with the positions of the first to sixth curvature radius portions 31B to 36B in the medial-lateral direction LR, respectively. That is to say, the seventh curvature radius portion 37B and the first curvature radius portion 31B are arranged in a line in the anterior-posterior direction FB. The twelfth curvature radius portion 42B and the sixth curvature radius portion 36B are arranged in a line in the anterior-posterior direction FB.

In this embodiment, the curvature radii of the seventh to twelfth curvature radius portions 37B to 42B (seventh to twelfth curvature radii r37B to r42B) in cross-sections perpendicular to the medial-lateral direction LR are set to be substantially the same as the corresponding seventh to twelfth curvature radii r37A to r42A of the femur sliding face 20A.

In the femur sliding face 20B, portions between adjacent curvature radius portions in the seventh to twelfth curvature radius portions 37B to 42B are formed as smooth faces. Thus, the entire second part 28B of the femur sliding face 20B is formed as a smoothly curved face. Furthermore, the first part 27B and the second part 28B form a smooth, continuous face, and the entire femur sliding face 20B is formed as a continuous, smooth face.

Referring to FIGS. 3(A), 6(A), and 6(B), this embodiment employs a shape in which, when the bending angle θ is relatively small when the femur component 2 is viewed from the back, the constraint force of the tibia component 3 with respect to the femur component 2 in the anterior-posterior direction FB and the medial-lateral direction LR (hereinafter also referred to simply as "constraint force") is increased, and the allowable degree of medial pivot motion is also increased. In this embodiment, medial pivot motion refers to motion of the tibia component 3 pivoting with respect to the femur component 2.

Specifically, a circle C37A, which forms the seventh curvature radius portion 37A, is shown in FIG. 6(B). Similarly, circles C38A, C39A, C40A, C41A, and C42A, which form the eighth to twelfth curvature radius portions 38A to 42A, respectively, are shown. A part of each of the circles C37A to C42A forms the corresponding one of the seventh to twelfth curvature radius portions 37A to 42A. Of the circles C37A to C42A, circles that are arranged closer to the component end side in the medial-lateral direction LR have central positions that are located further downward. Such a positional relationship is clear from the distance between an imaginary reference line L3, which passes through the upper end of the circle C37A and is parallel to the medial-lateral direction LR, and the respective circles C37A, C38A, C39A, C40A, C41A, and C42A.

Similarly, an arc A37B, which forms the seventh curvature radius portion 37B, is shown in FIG. 6(A). Similarly, arcs A38B to A42B, which form the eighth to twelfth curvature radius portions 38B to 42B, are shown in FIG. 6(A). The arcs A38B, A39B, A40B, A41B, and A42B form the seventh to twelfth curvature radius portions 37B to 42B, respectively. Of the arcs A37B to A42B, arcs that are arranged closer to the component end side in the medial-lateral direction LR have central positions that are located further downward.

The percentage by which the central position of a circle corresponds to the circles C37A to C42A shifts downward as the circle is arranged closer to the component end side in the medial-lateral direction LR is provided as a first percentage P1. The percentage by which the central position of an arc corresponds to the arcs A37B to A42B shifts downward as the arc is arranged closer to the component end side in the medial-lateral direction LR is provided as a second percentage P2. In this embodiment, the second percentage P2 is set to be larger than the first percentage P1 (P2>P1).

Referring to FIG. 3(A), in this embodiment, the posterior condylar portion 19A of the medial condyle 6A and the posterior condylar portion 19B of the lateral condyle 6B of the femur component 2 have, as a whole, four shoulder portions (first shoulder portion 51, second shoulder portion 52, third shoulder portion 53, and fourth shoulder portion 54) when viewed from the back (when the femur component 2 is viewed from the back).

The first shoulder portion 51 is a shoulder portion that is formed in a distal part of the posterior condylar portion 19B on the component end side on the lateral side (lateral condyle 6B) in the medial-lateral direction LR when viewed from the back. The second shoulder portion 52 is a shoulder portion that is formed in a proximal part of this posterior condylar portion 19B on the component end side when viewed from the back.

The third shoulder portion 53 is a shoulder portion that is formed in a distal part of the posterior condylar portion 19A on the component end side, on the medial side of the component (medial condyle 6A) in the medial-lateral direction LR when viewed from the back. The fourth shoulder portion 54 is a shoulder portion that is formed in a proximal part of this posterior condylar portion 19B on the component end side when viewed from the back.

The curvature radii of the first shoulder portion 51, the second shoulder portion 52, the third shoulder portion 53, and the fourth shoulder portion 54, when viewed from the back, are provided as r1, r2, r3, and r4, respectively. In this embodiment, a relationship of r2>r1 is prescripted with regard to the two curvature radii r1 and r2 on the lateral side in the medial-lateral direction LR.

Also, a relationship of r4>r3 is prescripted with regard to the two curvature radii r3 and r4 on the medial side in the medial-lateral direction LR. Furthermore, a relationship of r2>r4 is prescripted with regard to the two curvature radii r2 and r4 on the proximal side. In this embodiment, r2 is set to be approximately 110% of r4. Also, in this embodiment, a relationship of r1=r3 is prescripted with regard to the two curvature radii r1 and r3 on the distal side.

With the above configuration, in the femur component 2, the constraint force in the outer part of the femur component 2 in the medial-lateral direction LR becomes weaker than the constraint force in the inner part in the medial-lateral direction LR with an increase in the bending angle θ when the knee is in a state of deep flexion. As a result, the femur sliding face 20B provided on the lateral side in the medial-lateral direction LR can more smoothly slide with respect to the tibia sliding face 23B, and can perform medial pivot motion more smoothly.

Figure 7:
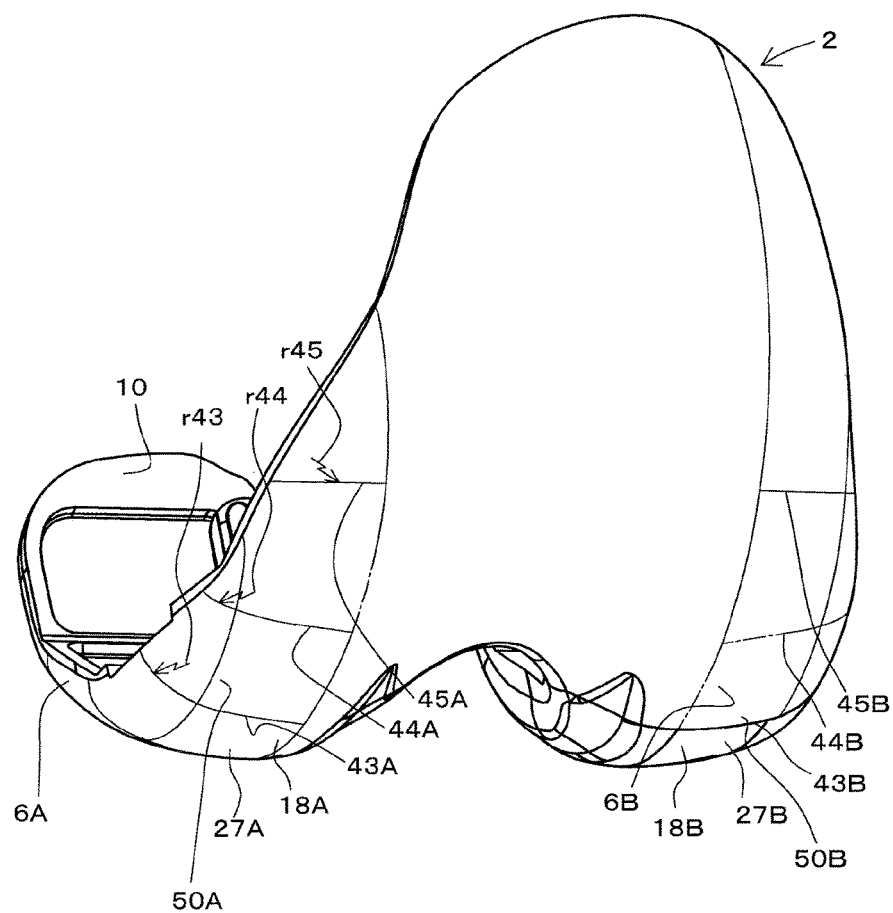
FIG. 7 is a perspective view for illustrating the shape of a front part of the femur component on a component end side.

FIG. 7 is a perspective view for illustrating the shape of front parts 50A and 50B of the femur component 2 on the component end side. Referring to FIG. 7, the femur component 2 has a shape for suppressing the occurrence of interference (contact) with the tibia component 3 and resulting in the femur component 2 being pressed rearward with an increase in the bending angle θ, when the bending angle θ is small (when θ is zero, or θ is several degrees). Specifically, the shapes of the front parts of the lateral condyle 6B and the medial condyle 6A of the femur component 2 on the component end side are curved to a great degree.

In this embodiment, the femur component 2 has the front parts 50A and 50B, which face forward when the patient has assumed an upright posture. The front part 50A is a front part of the medial condyle GA, and the front part 50B is a front part of the lateral condyle 6B. On the component end side, the curvature radii of the front parts 50A and 50B in parts extending in the medial-lateral direction LR of the patient vary so as to decrease continuously or stepwise toward the proximal side of the femur 101.

More specifically, a plurality of (at least three in this embodiment) curvature radii are set for each of the front parts 50A and 50B of the medial condyle 6A and the lateral condyle 6B. In this embodiment, the front parts 50A and 50B of the medial condyle 6A and the lateral condyle 6B have thirteenth curvature radius portions 43A and 43B, fourteenth curvature radius portions 44A and 44B, and fifteenth curvature radius portions 45A and 45B, respectively.

The thirteenth curvature radius portion 43A, the fourteenth curvature radius portion 44A, and the fifteenth curvature radius portion 45A of the medial condyle 6A have positions in the up-down direction UD that are aligned with those of the thirteenth curvature radius portion 43B, the fourteenth curvature radius portion 44B, and the fifteenth curvature radius portion 45B of the lateral condyle 6B, respectively. The thirteenth curvature radius portions 43A and 43B, the fourteenth curvature radius portions 44A and 44B, and the fifteenth curvature radius portions 45A and 45B extend straight in the medial-lateral direction LR.

The thirteenth curvature radius portions 43A and 43B, the fourteenth curvature radius portions 44A and 44B, and the fifteenth curvature radius portions 45A and 45B are arranged so as to face forward, and are spaced apart at predetermined intervals in the up-down direction UD. The thirteenth curvature radius portions 43A and 43B are arranged adjacent to front parts of the corresponding tibia sliding faces 23A and 23B when the bending angle θ is zero degrees. The fourteenth curvature radius portions 44A and 44B are arranged above (on the femur proximal side of) the thirteenth curvature radius portions 43A and 43B, and the fifteenth curvature radius portions 45A and 45B are arranged above the fourteenth curvature radius portions 44A and 44B.

The thirteenth to fifteenth curvature radius portions 43A, 43B, 44A, 44B, 45A, and 45B that are located further upward are configured to have a curvature radius whose percentage relative to the reference curvature radius rb is smaller. More specifically, in this embodiment, a curvature radius r43 of the thirteenth curvature radius portions 43A and 43B is set to be substantially the same as (98% of) the reference curvature radius rb. A curvature radius r44 of the fourteenth curvature radius portions 44A and 44B is set to be substantially half (42% of) the reference curvature radius rb. A curvature radius r45 of the fifteenth curvature radius portions 45A and 45B is set to be approximately 30% of the reference curvature radius rb.

Thus, the percentage of decrease from the curvature radius r43 of the thirteenth curvature radius portions 43A and 43B on the distal end side to the curvature radius r44 of the fourteenth curvature radius portions 44A and 44B is set to be larger than the percentage of decrease from the curvature radius r44 of the fourteenth curvature radius portions 44A and 44B to the curvature radius r45 of the fifteenth curvature radius portions 45A and 45B on the proximal side. With the above configuration, of the distal-end condylar portions 18A and 18B of the femur component 2, portions that are close to the tibia sliding faces 23A and 23B (particularly on the component end side) when an upright posture is assumed can be curved to a greater degree.

As a result, when the tibia component 3 in which the greatly-recessed tibia sliding faces 23A and 23B are employed comes into contact with the corresponding femur sliding faces 20A and 20B of the femur component 2, the femur component 2 and the tibia component 3 can maintain an appropriate positional relationship without interfering with each other when an upright posture is assumed.

The overview of the configuration of the femur component 2 is as described above. Next, the tibia component 3 will be described in more detail.

Figure 8A:
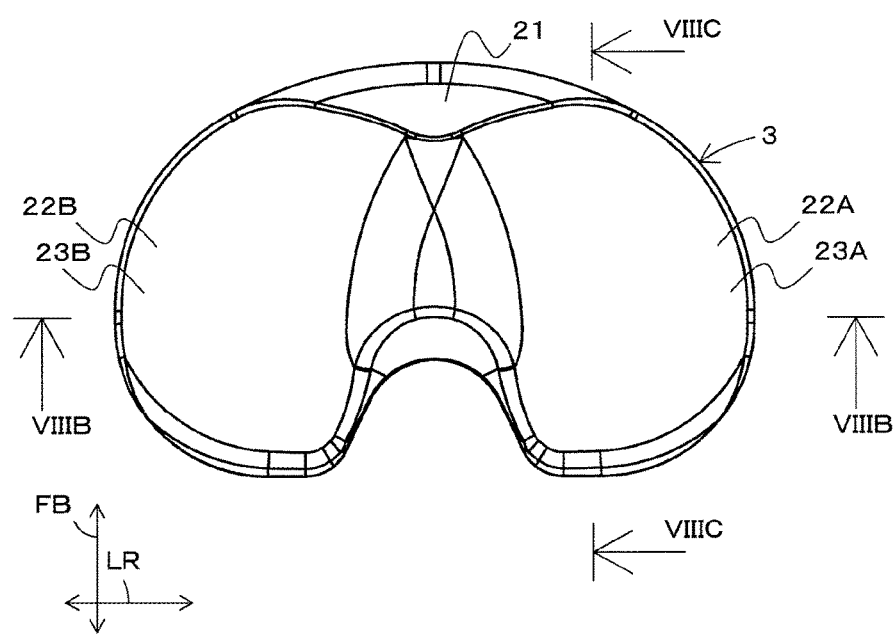
FIG. 8(A) is a plan view of the tibia component.
Figure 8B:
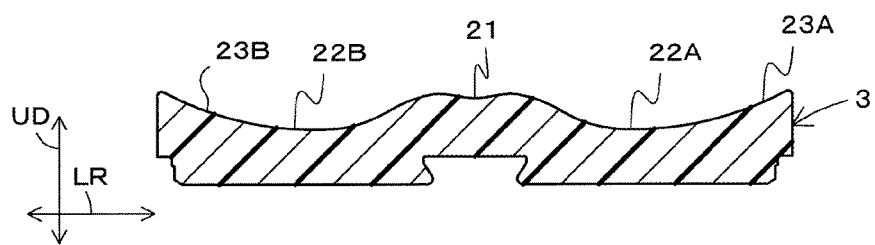
FIG. 8(B) is a cross-sectional view taken along a line VIIIB-VIIIB in FIG. 8(A).
Figure 8C:
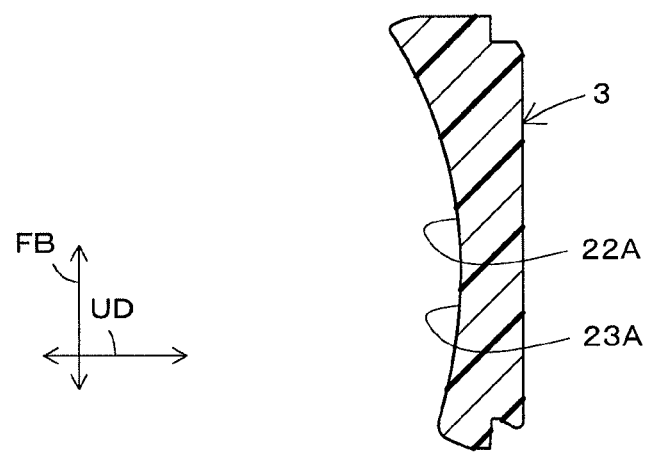
FIG. 8(C) is a cross-sectional view taken along a line VIIIC-VIIIC in FIG. 8(A).
Figure 9:
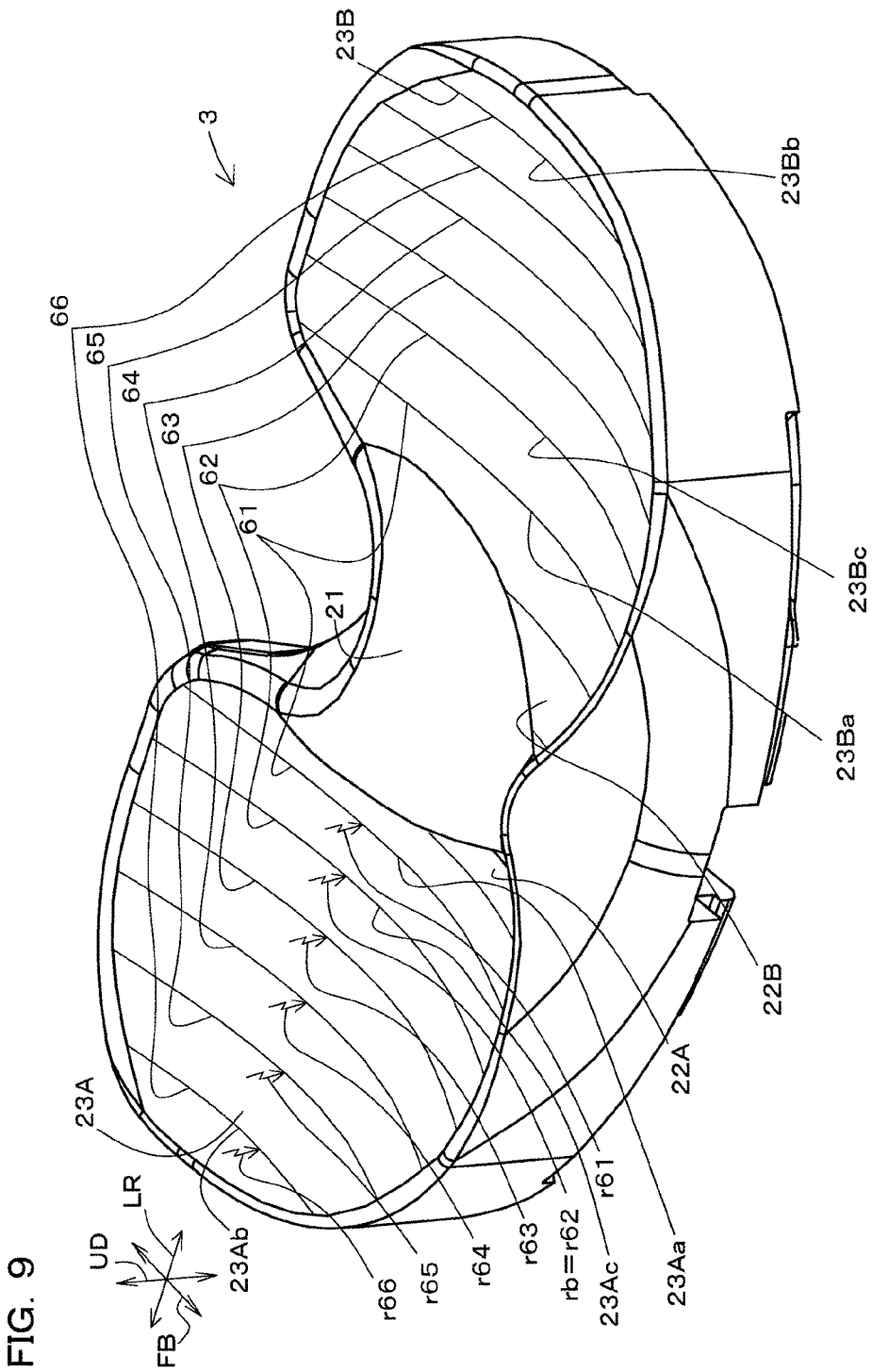
FIG. 9 is a perspective view of a tibia plate, with auxiliary lines for illustrating the curvature radii of tibia sliding faces added.

FIG. 8(A) is a plan view of the tibia component 3. FIG. 8(B) is a cross-sectional view taken along a line VIIIB-VIIIB in FIG. 8(A). FIG. 8(C) is a cross-sectional view taken along a line VIIIC-VIIIC in FIG. 8(A). FIG. 9 is a perspective view of the tibia component 3, with auxiliary lines for illustrating the curvature radii of the tibia sliding faces 23A and 23B added.

Referring to FIGS. 2, 5(A), 8(A) to 8(C), and 9, the tibia sliding faces 23A and 23B of the tibia component 3 are arranged side-by-side in the medial-lateral direction LR. In this embodiment, the tibia sliding faces 23A and 23B are formed in a symmetrical shape in the medial-lateral direction LR. As mentioned above, the tibia sliding face 23A is formed in the medial fossa 22A and is configured to slide against the femur sliding face 20A formed in the medial condyle 6A. The tibia sliding face 23B is formed in the lateral fossa 22B, and is configured to slide against the femur sliding face 20B formed in the lateral condyle 6B. The tibia sliding faces 23A and 23B are formed in the medial fossa 22A and the lateral fossa 22B, respectively, on the component end side in the medial-lateral direction LR.

In this embodiment, in the medial-lateral direction LR, first ends 23Aa and 23Ba of the tibia sliding faces 23A and 23B are provided at positions spaced apart from the bottom portions 23Ac and 23Bc of the medial fossa 22A and the lateral fossa 22B, respectively, toward the component central side by a predetermined amount. That is to say, the tibia sliding faces 23A and 23B include the bottom portions 23Ac and 23Bc of the medial fossa 22A and the lateral fossa 22B, respectively.

The bottom portions 23Ac and 23Bc are configured to come into contact with the first parts 27A and 27B of the corresponding femur sliding faces 20A and 20B when the bending angle θ is zero degrees. The first ends 23Aa and 23Ba of the tibia sliding faces 23A and 23B are arranged so as to come into contact with the corresponding femur sliding faces 20A and 20B when the bending angle θ is the maximum bending angle $θ_{max}$.

In this embodiment, in the medial-lateral direction LR, second ends 23Ab and 23Bb of the tibia sliding faces 23A and 23B are provided on the component end side in the medial fossa 22A and the lateral fossa 22B, respectively.

The tibia sliding faces 23A and 23B are each formed in a shape that includes a part of the hemisphere 26 (see FIG. 4). The tibia sliding faces 23A and 23B each have a shape that is obtained by cutting out a part of this hemisphere 26, face toward the component central side in the tibia component 3, and also face upward.

The tibia sliding faces 23A and 23B are provided as variable regions in which the curvature radius in a cross-section perpendicular to the medial-lateral direction LR varies in the medial-lateral direction LR, which serves as a predetermined direction.

In this embodiment, in respective regions between the bottom portions 23Ac and 23Bc of the tibia sliding faces 23A and 23B and the second ends 23Ab and 23Bb, the curvature radii of the tibia sliding faces 23A and 23B in cross-sections perpendicular to the medial-lateral direction LR decrease from the bottom portions 23Ac to 23Bc in the medial-lateral direction LR toward the component end side.

The tibia sliding faces 23A and 23B include regions in which the curvature radii of the tibia sliding faces 23A and 23B in cross-sections perpendicular to the anterior-posterior direction FB vary in the anterior-posterior direction, which serves as a predetermined direction.

A plurality of (at least six in this embodiment) curvature radii are set for each of the tibia sliding faces 23A and 23B. Specifically, in this embodiment, the tibia sliding faces 23A and 23B each have a first curvature radius portion 61, a second curvature radius portion 62, a third curvature radius portion 63, a fourth curvature radius portion 64, a fifth curvature radius portion 65, and a sixth curvature radius portion 66.

In the tibia sliding faces 23A and 23B, the first to sixth curvature radius portions 61 to 66 are arranged at substantially equal intervals in the medial-lateral direction LR, and extend in the anterior-posterior direction FB. The first curvature radius portions 61 are arranged respectively at the first ends 23Ac and 23Ba (on the component central side) of the tibia sliding faces 23A and 23B. The second curvature radius portions 62 pass through the corresponding bottom portions 23Ac and 23Bc. The sixth curvature radius portions 66 are arranged respectively at the second ends 23Ab and 23Bb (on the component end side) of the tibia sliding faces 23A and 23B.

The curvature radius of the first curvature radius portions 61 (first curvature radius r61) is set to be larger than the reference curvature radius rb (109% of the reference curvature radius rb in this embodiment). The curvature radius of the second curvature radius portions 62 (second curvature radius r62) is the same as the reference curvature radius rb. That is to say, in this embodiment, the reference curvature radius rb is the curvature radius of the bottom portions 23Ac and 23Bc in cross-sections that pass respectively through the bottom portions 23Ac and 23Bc of the tibia sliding faces 23A and 23B and are perpendicular to the medial-lateral direction LR. The curvature radius of the third curvature radius portions 63 (third curvature radius r63) is set to be approximately 90% (94% in this embodiment) of the reference curvature radius rb.

The curvature radius of the fourth curvature radius portions 64 (fourth curvature radius r64) is set to be approximately 90% (89% in this embodiment) of the reference curvature radius rb. The curvature radius of the fifth curvature radius portions 65 (fifth curvature radius r65) is set to be approximately 80% (84% in this embodiment) of the reference curvature radius rb. The curvature radius of the sixth curvature radius portions 66 (sixth curvature radius r66) is set to be approximately 80% (79% in this embodiment) of the reference curvature radius rb. In the tibia sliding faces 23A and 23B, portions between adjacent curvature radius portions in the first to sixth curvature radius portions 61 to 66 are formed as smooth faces. Thus, the entirety of the tibia sliding faces 23A and 23B are formed as smoothly curved faces.

In this embodiment, in the tibia sliding faces 23A and 23B, the sixth curvature radius r66 of the sixth curvature radius portions 66 that are closest to the component end side among the first to sixth curvature radius portions 61 to 66 is set to 85% or less of the second curvature radius r62 of the second curvature radius portions 62 that are closest to the bottom portions 23Ac and 23Bc among the first to sixth curvature radius portions 61 to 66. In this embodiment, the sixth curvature radius r66 is set to 79% of the second curvature radius r62 (reference curvature radius rb). In this embodiment, regarding the tibia sliding faces 23A and 23B, the curvature radius of the tibia sliding face 23A/23B between the bottom portion 23Ac/23Bc in the medial-lateral direction LR and a position corresponding to 5% of the overall length of the tibia sliding face 23A/23B in the component medial-lateral direction LR from the component end side is set to vary by 15% or more.

The overview of the configuration of the artificial knee joint implant 1 is as described above. Next, a description will be given of an example of operation of the artificial knee joint implant 1 performed with a bending motion, i.e. operation of the artificial knee joint implant 1 performed with a change in the bending angle θ.

Figure 10A:
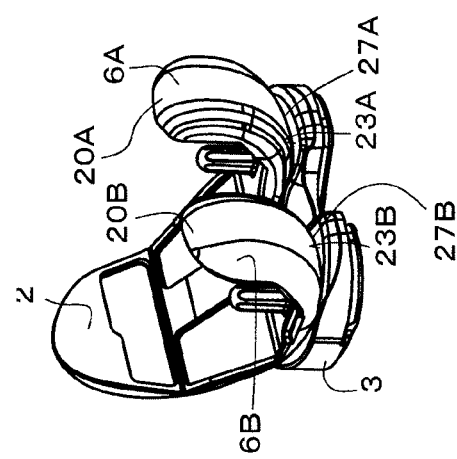
FIGS. 10(A) to 10(C) are perspective views for illustrating operation of the artificial knee joint implant.
Figure 10B:
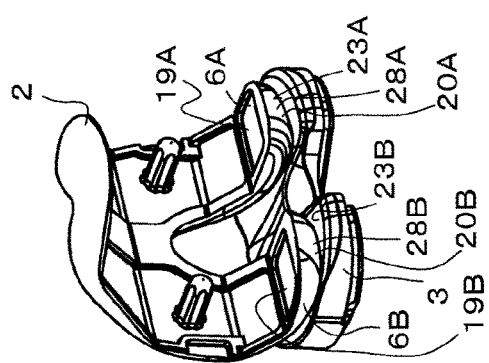
Figure 10C:
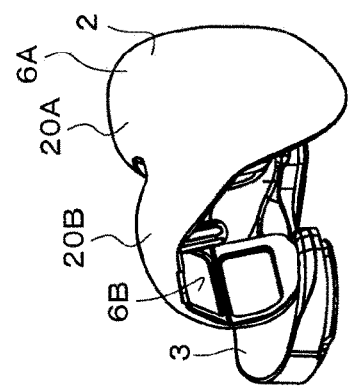

FIGS. 10(A) to 10(C) are perspective views for illustrating the operation of the artificial knee joint implant 1. FIG. 10(A) shows a state where the bending angle θ is zero degrees. FIG. 10(B) shows a state where the bending angle θ is 90 degrees. FIG. 10(C) shows a state in a range of the bending angle θ from 90 degrees to the maximum bending angle $\theta_{max}$.

Figure 11A:
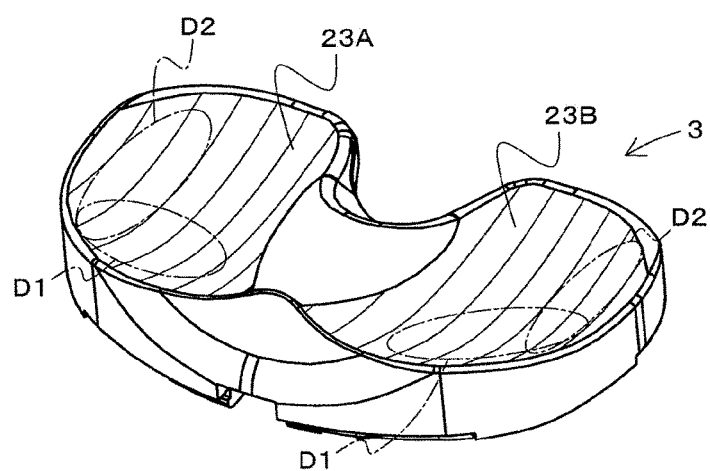
FIGS. 11(A) and 11(B) are perspective views of the tibia component.
Figure 11B:
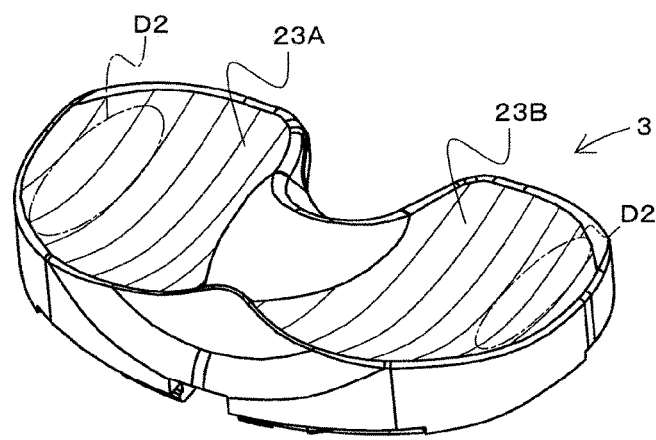

FIGS. 11(A) and 11(B) are perspective views of the tibia component 3. FIG. 11(A) shows sliding face regions D1 and D2 that constrain anterior-posterior and leftward-rightward movement of the femur sliding faces 20A and 20B when the bending angle θ is zero degrees (when an upright posture is assumed). FIG. 11(B) shows the sliding face regions D2 that constrain anterior-posterior and leftward-rightward movement of the femur sliding faces 20A and 20B when the bending angle θ has increased from zero degrees (when the knee is in a bent posture).

Referring to FIG. 10(A), when the bending angle θ is zero degrees, i.e. when the patient has assumed an upright posture, the first parts 27A and 27B of the femur sliding faces 20A and 20B are in contact with the bottom portions 23Ac and 23Bc of the corresponding tibia sliding faces 23A and 23B. When the bending angle θ has increased from zero degrees as a result of the patient performing a knee bending motion, the femur component 2 slides with respect to the tibia component 3, as shown in FIG. 10(B).

At this time, the second parts 28A and 28B of the femur sliding faces 20A and 20B slide against the corresponding tibia sliding faces 23A and 23B. As mentioned above, in the femur sliding faces sliding faces 20A and 20B, a relationship of r1<r2 and r3<r4 is prescripted with regard to the curvature radii of the shoulder portions 51 to 54 of the posterior condylar portions 19A and 19B when viewed from the back.

For this reason, as shown in FIGS. 10(B) and 10(C), the femur sliding face 20B of the lateral condyle 6B is displaced rearward with respect to the femur sliding face 20A of the medial condyle 6A with an increase in the bending angle θ. That is to say, the tibia component 3 undergoes medial pivot motion, i.e. is displaced so as to pivot with respect to the femur component 2.

Here, the magnitude of the constraint force of the femur component 2 and the tibia component 3 in the anterior-posterior direction FB and the medial-lateral direction LR will be described in more detail. Referring to FIGS. 10(A) and 11(A), the curvature radii of the femur sliding faces 20A and 20B are set to be smaller on the component end side, as mentioned above. Similarly, the curvature radii of the tibia sliding faces 23A and 23B are set to be smaller on the component end side.

When the bending angle θ is relatively small, the femur sliding faces 20A and 20B are in contact with the front parts of the corresponding tibia sliding faces 23A and 23B and most parts of the tibia sliding faces 23A and 23B on the component end side (regions D1 and regions D2), and have a large constraint force in the anterior-posterior direction FB and the medial-lateral direction LR.

As shown in FIGS. 10(B), 10(C), and 11(B), when the bending angle θ is larger than zero degrees, the femur sliding faces 20A and 20B are received by parts of the corresponding tibia sliding faces 23A and 23B with a small curvature radius on the component end side (regions D2). As a result, the femur sliding faces 20A and 20B have a large constraint force in the anterior-posterior direction FB and in the medial-lateral direction LR. That is to say, the femur sliding faces 20A and 20B are held by the tibia sliding faces 23A and 23B with a large constraint force regardless of the bending angle θ.

The high allowable degree of medial pivot motion of the tibia component 3 with respect to the femur component 2 will now be described in more detail. As shown in FIGS. 5, 6, and 11(A), the curvature radii of the femur sliding faces 20A and 20B are set to be larger on the component central side. Similarly, the curvature radii of the tibia sliding faces 23A and 23B are set to be larger on the component central side.

When the bending angle θ increases from zero degrees, component central parts of the femur sliding faces 20A and 20B with larger curvature radii slide against the corresponding tibia sliding faces 23A and 23B on the component central side where the curvature radii are larger. Thus, the femur sliding faces 20A and 20B can smoothly slide with respect to the corresponding tibia sliding faces 23A and 23B. Accordingly, the allowable degree of medial pivot motion of the tibia component 3 with respect to the femur 101 can be further increased regardless of the bending angle θ.

As described above, in the artificial knee joint implant 1, the femur sliding faces 20A and 20B and the tibia sliding faces 23A and 23B each have a variable region in which the curvature radius varies in the medial-lateral direction LR. Also, the femur sliding faces 20A and 20B and the tibia sliding faces 23A and 23B each have a variable region in which the curvature radius varies in the anterior-posterior direction FB. With this configuration, the contact state between the sliding faces 20A and 20B of the femur component 2 and the sliding faces 23A and 23B of the tibia component 3, respectively, can be varied in accordance with the bending angle θ of the patient's knee. As a result, regardless of the bending angle θ, the constraint force of the femur component 2 and the tibia component 3 in the anterior-posterior direction FB and the left-right direction (medial-lateral direction LR) of the patient can be increased, and the allowable degree of medial pivot motion can be increased. It is thus possible to realize an artificial knee joint implant 1 capable of increasing the constraint force of the femur component 2 and the tibia component 3 in the anterior-posterior direction FB and the left-right direction (medial-lateral direction LR) of the patient, and increasing the allowable degree of medial pivot motion. In addition, with the femur component 2 and the tibia component 3, when the knee is in a state of deep flexion, medial pivot motion and rearward movement can be further promoted on the lateral side in the medial-lateral direction LR than on the medial side with an increase in the bending angle θ.

In the artificial knee joint implant 1, in all of the femur sliding faces 20A and 20B and the tibia sliding faces 23A and 23B, the curvature radius in a cross-section perpendicular to the medial-lateral direction LR varies in the medial-lateral direction LR. This configuration indicates that a simple configuration is employed for the femur sliding faces 20A and 20B and the tibia sliding faces 23A and 23B in which the curvature radius is varied in the medial-lateral direction LR. Thus, regardless of the bending angle θ, the constraint force can be increased, and the allowable degree of medial pivot motion can also be increased.

In the artificial knee joint implant 1, in at least a part of the tibia sliding faces 23A and 23B (regions on the component end side with respect to the bottom portions 23Ac and 23Bc), the curvature radii of the tibia sliding faces 23A and 23B decrease from the bottom portions 23Ac and 23Bc of the tibia sliding faces 23A and 23B in the medial-lateral direction LR toward the component end side. With this configuration, when the bending angle θ of the patient's knee is relatively small, the femur sliding faces 20A and 20B can come into contact with the front parts of the tibia sliding faces 23A and 23B and most parts of the tibia sliding faces 23A and 23B on the component end side (region D1 and region D2). Accordingly, a large constraint force can be secured. When the bending angle θ is relatively large, the femur sliding faces 20A and 20B are received by parts of the tibia sliding faces 23A and 23B on the component end side with small curvature radii (regions D2). Thus, a large constraint force can be secured. That is to say, the femur sliding faces 20A and 20B are held by the tibia sliding faces 23A and 23B with a large constraint force regardless of the bending angle θ. In addition, due to the curvature radii of the bottom portions 23Ac and 23Bc of the tibia sliding faces 23A and 23B being larger and the curvature radii of the tibia sliding faces 23A and 23B on the component end side being smaller, the allowable degree of medial pivot motion can be further increased regardless of the bending angle.

In the artificial knee joint implant 1, in the tibia sliding faces 23A and 23B, the curvature radius between the bottom portion 23Ac/23Bc of the tibia sliding face 23A/23B in the medial-lateral direction LR and a position corresponding to 5% of the overall length of the tibia sliding face 23A/23B in the component medial-lateral direction LR from the component end side is set to vary by 15% or more. By setting the relationship regarding the curvature radii of the tibia sliding faces 23A and 23B as described above, a significant effect of synergistically increasing both the allowable degree of medial pivot motion and the constraint force can be exhibited.

In the artificial knee joint implant 1, the femur sliding faces 20A and 20B and the tibia sliding faces 23A and 23B each have a region in which the curvature radius varies in the anterior-posterior direction FB, as mentioned above. This configuration can vary the contact state between the femur sliding faces 20A and 20B and the tibia sliding faces 23A and 23B with a change in the bending angle θ. As a result, regardless of the bending angle θ, the constraint force can be increased, and the allowable range of medial pivot motion can also be increased.

In the artificial knee joint implant 1, the curvature radii of the first parts 27A and 27B of the distal-end condylar portions 18A and 18B are set to be larger than the curvature radii of the second parts 28A and 28B of the corresponding posterior condylar portions 19A and 19B in cross-sections perpendicular to the medial-lateral direction LR. This configuration can make the shape of the femur sliding faces 20A and 20B more similar to the shape of a normal knee in a human body.

In the artificial knee joint implant 1, in at least a part of the femur sliding faces 20A and 20B (in this embodiment, the entire femur sliding faces 20A and 20B), the curvature radii of the femur sliding faces 20A and 20B in cross-sections perpendicular to the medial-lateral direction LR decrease toward the component end side from the bottom portions 20Ac and 20Bc of the femur sliding faces 20A and 20B in the medial-lateral direction LR. With this configuration, when the knee is bent, the femur sliding faces 20A and 20B (second parts 28A and 28B) of the posterior condylar portions 19A and 19B are received on the component end side in the corresponding tibia sliding faces 23A and 23B. Thus, it is possible to avoid impingement between the femur component 2 and the tibia component 3 due to medial pivot motion, while suppressing a decrease in the constraint force. Accordingly, a decrease in the constraint force can be suppressed, and the allowable degree of medial pivot motion can be further increased.

In the artificial knee joint implant 1, in the femur sliding faces 20A and 20B (first parts 27A and 27B) in the distal-end condylar portions 18A and 18B, the curvature radius between the bottom portion 20Ac/20Bc of the femur sliding face 20A/20B in the medial-lateral direction LR and the position corresponding to 5% of the overall length of the femur sliding face 20A/20B in the component medial-lateral direction LR from the component end side is set to vary by 45% or more. In the femur sliding faces 20A and 20B (second parts 28A and 28B) of the posterior condylar portions 19A and 19B, the curvature radius between the bottom portion 20Ac/20Bc of the femur sliding face 20A/20B in the medial-lateral direction LR and the position corresponding to 5% of the overall length of the femur sliding face 20A/20B in the component medial-lateral direction LR from the component end side is set to vary by 5% or more. By setting the relationship regarding the curvature radii of the respective parts of the femur sliding faces 20A and 20B as described above, a significant effect of synergistically increasing both the allowable degree of medial pivot motion and the constraint force can be exhibited.

In the artificial knee joint implant 1, when the curvature radii of the first shoulder portion 51 and the second shoulder portion 52 are r1 and r2, respectively, r2 is larger than r1 when the femur component 2 is viewed from the back. With this configuration, when the bending angle of the knee is large (when the knee is in a state of deep flexion), the portions of the femur sliding faces 20A and 20B that come into contact with the tibia sliding faces 23A and 23B change from the first shoulder portion 51 to the second shoulder portion 52 with an increase in the bending angle θ. Thus, the femur sliding faces 20A and 20B can be brought into contact with the corresponding tibia sliding faces 23A and 23B so as to further promote medial pivot motion and rearward movement. As a result, with an increase in the bending angle when the knee is in a state of deep flexion, the allowable degree of medial pivot motion can be further increased, and rearward movement can be promoted.

In the artificial knee joint implant 1, when the curvature radii of the third shoulder portion 53 and the fourth shoulder portion 54 are r3 and r4, respectively, r4 is larger than r3 when the femur component 2 is viewed from the back. With this configuration, when the knee is in a state of deep flexion, the portions of the femur sliding faces 20A and 20B that come into contact with the tibia sliding faces 23A and 23B change from the third shoulder portion 53 to the fourth shoulder portion 54 with an increase in the bending angle θ. Thus, the femur sliding faces 20A and 20B can be brought into contact with the corresponding tibia sliding faces 23A and 23B so as to further promote medial pivot motion and rearward movement. As a result, with an increase in the bending angle when the knee is in a state of deep flexion, the allowable degree of medial pivot motion can be further increased, and rearward movement can be promoted.

In the artificial knee joint implant 1, r2 is set to be larger than r4. With this configuration, when the knee is in a state of deep flexion, the femur sliding faces 20A and 20B can be brought into contact with the corresponding tibia sliding faces 23A and 23B so as to further promote medial pivot motion on the lateral side than on the medial side, with an increase in the bending angle θ. As a result, the allowable degree of medial pivot motion can be further increased.

In the artificial knee joint implant 1, on the component end side in the front parts 50A and 50B of the femur component 2, the curvature radii (r43, r44, and r45) of portions (thirteenth curvature radius portion 43A, fourteenth curvature radius portion 44A, and fifteenth curvature radius portion 45A) that extend in the medial-lateral direction LR of the patient vary so as to decrease continuously or stepwise toward the proximal side of the femur 101. With this configuration, the shapes of the front portions 50A and 50B of the femur component 2 on the component end side can be curved to a greater degree. Thus, it is possible to avoid, when the patient has assumed an upright posture, the component end side in the front parts 50A and 50B of the femur component 2 interfering with the corresponding concave tibia sliding faces 23A and 23B of the tibia component 3. As a result, when the patient has assumed an upright posture, an appropriate positional relationship can be maintained without the femur component 2 interfering with the tibia component 3.

An embodiment of the present invention has been described above. However, the present invention is not limited to the above-described embodiment, and can be modified in various manners within the scope of the claims.

INDUSTRIAL APPLICABILITY

The present invention can be widely applied as an artificial knee joint implant to be used in surgery to replace a knee joint of a patient with an artificial knee joint.

DESCRIPTIONS OF REFERENCE NUMERALS

1 Artificial knee joint implant
2 Femur component
3 Tibia component
18A, 18B Distal-end condylar portion (condylar portion)
19A, 19B Posterior condylar portion (condylar portion)
20A, 20B Femur sliding face (variable region)
23A, 23B Tibia sliding face (variable region)
43A, 43B Thirteenth curvature radius portion (portion extending in the medial-lateral direction)
44A, 44B Fourteenth curvature radius portion (portion extending in the medial-lateral direction)
45A, 45B Fifteenth curvature radius portion (portion extending in the medial-lateral direction)
  50A, 50B Front part
  51~54 Shoulder portion
101 Femur
102 Distal portion
103 Tibia
104 Proximal portion
FB Anterior-posterior direction (predetermined direction)
LR Medial-lateral direction (predetermined direction)
UD Up-down direction
r1, r2, r3, r4 Curvature radii of shoulders
r31A, r31B Curvature radius (curvature radius of femur sliding face in distal-end condylar portion on component central side)
r36A, r36b Curvature radius (curvature radius of femur sliding face in distal-end condylar portion on component end side)
r37A, r37b Curvature radius (curvature radius of femur sliding face in posterior condylar portion on component central side)
r42A, r42b Curvature radius (curvature radius of femur sliding face in posterior condylar portion on component end side)
r43 Curvature radius of portion extending in the medial-lateral direction
r44 Curvature radius of portion extending in the medial-lateral direction
r45 Curvature radius of portion extending in the medial-lateral direction
r62 Curvature radius (curvature radius of bottom portion of tibia sliding face)
r66 Curvature radius (curvature radius of tibia sliding face on component end side)

The invention claimed is:

1. An artificial knee joint implant comprising:
a femur component to be fixed to a distal portion of a femur of a patient; and
a tibia component to be fixed to a proximal portion of a tibia of the patient,
wherein the femur component includes a convex femur sliding face,
the tibia component has a concave tibia sliding face configured to face the femur sliding face, and
the femur sliding face and the tibia sliding face each include a surface, each surface having different curvature radii at separate locations in a medial-lateral direction, each of the different curvature radii extending in a sagittal plane perpendicular to the medial-lateral direction,
wherein, the surface of the femur sliding face includes a first condylar portion, extending in the medial-lateral direction, at a distal portion of the femur component,
a first curvature radius, at a bottommost location of a curved region of the first condylar portion, is greater than a second curvature radius, at a location corresponding to 5% of an overall length of the curved region from a femur component end side,
the surface of the tibia sliding face includes a curved tibia region extending in the medial-lateral direction,
a third curvature radius, at a bottommost location along the curved tibia region is greater than a fourth curvature radius at a location corresponding to 5% of an overall length of the tibia sliding face from a tibia component end side, and
a first percentage of the amount of change in curvature radius from the first curvature radius to the second curvature radius is equal to or greater than a second percentage of the amount of change from the third curvature radius to the fourth curvature radius.

2. The artificial knee joint implant according to claim 1, wherein, the second percentage is 15% or more.

3. The artificial knee joint implant according to claim 1, wherein each surface also has different curvature radii at separate locations in an anterior-posterior direction.

4. The artificial knee joint implant according to claim 3, wherein the first condylar portion is configured to be attached to a distal end of the femur, and the femur component includes a second condylar portion, extending in the medial-lateral direction, at a posterior side of the femur component rearward of the first condylar portion,
the femur sliding face is formed so as to span both the first condylar portion and the second condylar portion, and
in a cross-section extending in a sagittal plane perpendicular to the medial-lateral direction, the first curvature radius of the curved region of the first condylar portion is larger than a fifth curvature radius at a bottommost location of a curved region of the second condylar portion of the femur sliding face.

5. The artificial knee joint implant according to claim 4, wherein, the first percentage is 45% or more,
a sixth curvature radius at a location corresponding to 5% of an overall length of the curved region of the second condylar portion from the femur component end side, is smaller than the fifth curvature radius at the bottommost location of the curved region of the second condylar portion of the femur sliding face, and
a third percentage of the amount of change in curvature radius from the fifth curvature radius to the sixth curvature radius is 5% or more.

6. The artificial knee joint implant according to claim 1, wherein
a pair of condylar components are arranged side-by-side in the medial-lateral direction, and, for a first condylar component on a lateral side of the femur component, when a curvature radius of a distal shoulder portion joining a distal end side condylar portion and a lateral end side condylar portion is r1 and a curvature radius of a proximal shoulder portion joining a proximal end side condylar portion and the lateral end side condylar portion is r2, r2 is larger than r1 when the femur component is viewed from a posterior of the femur component.

7. The artificial knee joint implant according to claim 6, wherein, for a second condylar component on a medial side of the femur component, when a curvature radius of a distal shoulder portion joining a distal end side condylar portion and a medial end side condylar portion is r3 and a curvature radius of a proximal shoulder portion joining a proximal end side condylar portion and the medial end side condylar portion is r4, r4 is larger than r3 when the femur component is viewed from a posterior of the femur component.

8. The artificial knee joint implant according to claim 7, wherein r2 is larger than r4.

9. The artificial knee joint implant according to claim 1, wherein the femur component has an anterior part that faces forward when the patient has assumed an upright posture, and
in the anterior part, on the femur component end side, a curvature radius of a portion extending in the medial-lateral direction of the patient varies so as to decrease continuously or stepwise toward a proximal side of the femur.

\* \* \* \* \*